United States Patent
Nomoto et al.

(10) Patent No.: US 7,235,396 B2
(45) Date of Patent: Jun. 26, 2007

(54) BACTERIUM FOR PRODUCING POLYHYDROXYALKANOATE HAVING POLYHYDROXYALKANOATE DEPOLYMERASE GENE DISRUPTED AND METHOD FOR PRODUCING POLYHYDROXYALKANOATE USING THE SAME

(75) Inventors: Tsuyoshi Nomoto, Komae (JP); Tetsuya Yano, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/341,665

(22) Filed: Jan. 30, 2006

(65) Prior Publication Data

US 2006/0172400 A1   Aug. 3, 2006

(30) Foreign Application Priority Data

Jan. 31, 2005   (JP) .............................. 2005-023975

(51) Int. Cl.
*C12N 1/20*   (2006.01)
*C12P 7/62*   (2006.01)
*C12Q 3/07*   (2006.01)
*C12N 15/74*   (2006.01)
*C12N 1/21*   (2006.01)

(52) U.S. Cl. ............................. 435/253.3; 435/252.34; 435/252.33; 435/69.1; 435/135; 435/252.3; 536/23.2

(58) Field of Classification Search ..................... None
See application file for complete search history.

(56) References Cited

U.S. PATENT DOCUMENTS

2006/0172394 A1* 8/2006 Kozaki et al. .............. 435/117
2006/0172398 A1* 8/2006 Nomoto et al. ............. 435/135
2006/0172399 A1* 8/2006 Nomoto et al. ............. 435/135

* cited by examiner

*Primary Examiner*—Rebecca E. Prouty
*Assistant Examiner*—Md. Younus Meah
(74) *Attorney, Agent, or Firm*—Fitzpatrick, Cella, Harper & Scinto

(57) ABSTRACT

The objective of the present invention is to provide a bacterium for producing polyhydroxyalkanoate with improved productivity. To achieve above objective, the gene coding for the polyhydroxyalkanoate depolymerase of the bacterium for producing polyhydroxyalkanoate is disrupted to improve the productivity of polyhydroxyalkanoate.

2 Claims, 3 Drawing Sheets

SEQUENCE LISTING

<160> NUMBER OF SEQ ID NOS: 15

<210> SEQ ID NO 1
<211> LENGTH: 855
<212> TYPE: DNA
<213> ORGANISM: Pseudomonas sp. YN21

<400> SEQUENCE: 1

```
atgccgcaac cgttcatatt ccgcaccgtc gacctggatg gccagaccct ccgcacggcg     60
gtgcgccccg gcaagcctca cttgacgccc ttgctgattt caacggcat cggcgccaac    120 ctggagctgg tgtttccgtt cgtcgcagcg ctggacccgg acctcgaagt catcgccttc    180
gacgtacccg gtgttggcgg ttcatcgacg cccaatcgtc catatcgttt cccaggcctg    240
gcaaagctca cggcacgcat gctcgactac ctcgattacg ggcgagtcaa cgtgatcggc    300
gtgtcatggg gtggcgccct tgcgcaacag ttcgcctatg actatccaga gcggtgcaag    360
aagctggtcc tggcagcgac agccgcgggt acggtgatgg tgccgggcaa gccgaaagtc    420
ttgtggatga tggccagccc acgacggtac atccagccat cccacgtgat ccgcattgcg    480
ccgatgatct acggcggctc gttccgtcgc gacccgacgc tggctgcaag ccatgcggca    540
aaggtccgtt cggcgggcaa gctcggttac tactggcaac tgttcgccgg cttcggctgg    600
accagcatcc actggctgca caagatcaat cagccgaccc tggtcctggc cggcgacgac    660
gaccccttga ttccgttggt caacatgcgc ttgctggcct ggcggatccc caatgcccaa    720
ctgcacatca tcgacgacgg ccatctgttc ttgatcaccc gggccgaagc ggtggcaccg    780
atcatcatga agttccttga agaggagcgc cagcgtgcgg tgatgcaccc gcatccggcg    840
ccactgggtg gctga                                                     855
```

<210> SEQ ID NO 2
<211> LENGTH: 30
<212> TYPE: DNA
<213> ORGANISM: Artificial Sequence
<220> FEATURE:
<223> OTHER INFORMATION: PCR primer, phaZ-f1

<400> SEQUENCE: 2

```
accgtcgagc tcgatggcca gaccctccgc                                      30
```

<210> SEQ ID NO 3
<211> LENGTH: 30
<212> TYPE: DNA
<213> ORGANISM: Artificial Sequence
<220> FEATURE:
<223> OTHER INFORMATION: PCR primer, phaZ-r1

<400> SEQUENCE: 3
gcaccgctct agatagtcat aggcgaactg                                        30

<210> SEQ ID NO 4
<211> LENGTH: 30
<212> TYPE: DNA
<213> ORGANISM: Artificial Sequence
<220> FEATURE:
<223> OTHER INFORMATION: PCR primer, phaZ-r2

<400> SEQUENCE: 4
gcattgggga tccgccaggc cagcaagcgc                                        30

<210> SEQ ID NO 5
<211> LENGTH: 30
<212> TYPE: DNA
<213> ORGANISM: Artificial Sequence
<220> FEATURE:
<223> OTHER INFORMATION: PCR primer, pEX-f1

<400> SEQUENCE: 5
atccctagag ctcggcgtaa tcatggtcat                                        30

<210> SEQ ID NO 6
<211> LENGTH: 30
<212> TYPE: DNA
<213> ORGANISM: Artificial Sequence
<220> FEATURE:
<223> OTHER INFORMATION: PCR primer, pEX-r1

<400> SEQUENCE: 6
ttgcagcgga tcccccttc gccagctggc                                         30

<210> SEQ ID NO 7
<211> LENGTH: 6393
<212> TYPE: DNA
<213> ORGANISM: Artificial Sequence
<220> FEATURE:
<223> OTHER INFORMATION: plasmid, pEX-phaZ

<400> SEQUENCE: 7
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataatcg gcattttctt ttgcgttttt atttgttaac tgttaattgt ccttgttcaa     240
ggatgctgtc tttgacaaca gatgttttct tgcctttgat gttcagcagg aagctaggcg     300
caaacgttga ttgtttgtct gcgtagaatc ctctgtttgt catatagctt gtaatcacga     360 cattgttttcc tttcgcttga ggtacagcga agtgtgagta agtaaaggtt acatcgttag     420
gatcaagatc catttttaac acaaggccag ttttgttcag cggcttgtat gggccagtta     480
aagaattaga aacataacca agcatgtaaa tatcgttaga cgtaatgccg tcaatcgtca     540
tttttgatcc gcgggagtca gtgaacagat accatttgcc gttcatttta aagacgttcg     600

-continued

```
cgcgttcaat ttcatctgtt actgtgttag atgcaatcag cggtttcatc acttttttca    660
gtgtgtaatc atcgtttagc tcaatcatac cgagagcgcc gtttgctaac tcagccgtgc    720
gttttttatc gctttgcaga agttttttgac tttcttgacg gaagaatgat gtgcttttgc   780
catagtatgc tttgttaaat aaagattctt cgccttggta gccatcttca gttccagtgt    840
ttgcttcaaa tactaagtat ttgtggcctt tatcttctac gtagtgagga tctctcagcg    900
tatggttgtc gcctgagctg tagttgcctt catcgatgaa ctgctgtaca ttttgatacg    960
tttttccgtc accgtcaaag attgattat aatcctctac accgttgatg ttcaaagagc    1020
tgtctgatgc tgatacgtta acttgtgcag ttgtcagtgt ttgtttgccg taatgtttac    1080
cggagaaatc agtgtagaat aaacggattt ttccgtcaga tgtaaatgtg gctgaacctg    1140
accattcttg tgtttggtct tttaggatag aatcatttgc atcgaatttg tcgctgtctt    1200
taaagacgcg gccagcgttt ttccagctgt caatagaagt ttcgccgact ttttgataga    1260
acatgtaaat cgatgtgtca tccgcatttt taggatctcc ggctaatgca aagacgatgt    1320
ggtagccgtg atagtttgcg acagtgccgt cagcgttttg taatggccag ctgtcccaaa    1380
cgtccaggcc ttttgcagaa agatatttt taattgtgga cgaatcgaac tcaggaactt    1440 gatattttc attttttttgc tgttcaggga tttgcagcat atcatggcgt gtaatatggg    1500
aaatgccgta tgtttcctta tatggctttt ggttcgtttc tttcgcaaac gcttgagttg    1560
cgcctcctgc cagcagtgcg gtagtaaagg ttaatactgt tgcttgtttt gcaaactttt    1620
tgatgttcat cgttcatgtc tccttttta tgtactgtgt tagcggtctg cttcttccag    1680
ccctcctgtt tgaagatggc aagttagtta cgcacaataa aaaagacct aaaatatgta     1740 aggggtgacg ccaaagtata cactttgccc tttacacatt ttaggtcttg cctgctttat    1800
cagtaacaaa cccgcgcgat ttacttttcg acctcattct attagactct cgtttggatt    1860
gcaactggtc tattttcctc ttttgtttga tagaaaatca taaaaggatt tgcagactac    1920
gggcctaaag aactaaaaaa tctatctgtt tcttttcatt ctctgtattt tttatagttt    1980
ctgttgcatg gcataaaagt tgccttttta atcacaattc agaaaatatc ataatatctc    2040
atttcactaa ataatagtga acggcaggta tatgtgatgg gttaaaaagg atcgatcctc    2100
tagctagagt cgatcttcgc cagcagggcg aggatcgtgg catcaccgaa ccgcgccgtg    2160
cgcgggtcgt cggtgagcca gagtttcagc aggccgccca ggcggcccag gtcgccattg    2220
atgcgggcca gctcgcggac gtgctcatag tccacgacgc ccgtgatttt gtagccctgg    2280
ccgacggcca gcaggtaggc cgacaggctc atgccggccg ccgccgcctt ttcctcaatc    2340
gctcttcgtt cgtctggaag gcagtacacc ttgataggtg ggctgccctt cctggttggc    2400
ttggtttcat cagccatccg cttgccctca tctgttacgc cggcggtagc cggccagcct    2460
cgcagagcag gattcccgtt gagcaccgcc aggtgcgaat aagggacagt gaagaaggaa    2520
cacccgctcg cgggtgggcc tacttcacct atcctgcccg gctgacgccg ttggatacac    2580
caaggaaagt ctacacgaac cctttggcaa atcctgtat atcgtgcgaa aaaggatgga    2640
tataccgaaa aaatcgctat aatgacccg aagcagggtt atgcagcgga aaagcgctgc    2700
ttccctgctg ttttgtggaa tatctaccga ctggaaacag gcaaatgcag gaaattactg    2760
aactgagggg acaggcgaga gacgatgcca agagctacca ccgacgagct ggccgagtgg    2820
gttgaatccc gcgcggccaa gaagcgccgg cgtgatgagg ctgcggttgc gttcctggcg    2880 gtgagggcg atgtcgatat gcgtaaggag aaaataccgc atcaggcgca tgcatatttg    2940
aatgtattta gaaaaataaa caaaaagagt ttgtagaaac gcaaaaaggc catccgtcag    3000
```

```
gatggccttc tgcttaattt gatgcctggc agtttatggc gggcgtcctg cccgccaccc    3060
tccgggccgt tgcttcgcaa cgttcaaatc cgctcccggc ggatttgtcc tactcaggag    3120
agcgttcacc gacaaacaac agataaaacg aaaggcccag tctttcgact gagcctttcg    3180
ttttatttga tgcctggcag ttccctactc tcgcatgggg agaccccaca ctaccatcgg    3240
cgctacggcg tttcacttct gagttcggca tggggtcagg tgggaccacc gcgctactgc    3300
cgccaggcaa attctgtttt atcagaccgc ttctgcgttc tgatttaatc tgtatcaggc    3360
tgaaaatctt ctctcatccg ccaaaacagc caagctcgcc attcgccatt caggctgcgc    3420
aactgttggg aagggcgatc ggtgcgggcc tcttcgctat tacgccagct ggcgaaaggg    3480
ggatgccgca ggccagcaag cgcatgttga ccaacggaat caaggggtcg tcgtcgccgg    3540
ccaggaccag ggtcggctga ttgatcttgt gcagccagtg gatgctggtc cagccgaagc    3600
cggcgaacag ttgccagtag taaccgagct tgcccgccga acggaccttt gccgcatggc    3660
ttgcagccag cgtcgggtcg cgacggaacg agccgccgta gatcatcggc gcaatgcgga    3720
tcacgtggga tggctggatg taccgtcgtg ggctggccat catccacaag actttcggct    3780
tgcccggcac catcaccgta cccgcggctg tcgctgccag gaccagcttc ttgcaccgct    3840
ctagatagtc ataggcgaac tgttgcgcaa gggcgccacc ccatgacacg ccgatcacgt    3900
tgactcgccc gtaatcgagg tagtcgagca tgcgtgccgt gagctttgcc aggcctggga    3960
aacgatatgg acgattgggc gtcgatgaac cgccaacacc gggtacgtcg aaggcgatga    4020
cttcgaggtc cgggtccagc gctgcgacga acggaaacac cagctccagg ttggcgccga    4080
tgccgttgaa atcagcaagg gcgtcaagt gaggcttgcc ggggcgcacc gccgtgcgga    4140
gggtctggcc atcgagctcg gcgtaatcat ggtcatagct gtttcctgtg tgaaattgtt    4200
atccgctcac aattccacac aacatacgag ccggaagcat aaagtgtaaa gcctggggtg    4260
cctaatgagt gagctaactc acattaattg cgttgcgctc actgcccgct ttccagtcgg    4320
gaaacctgtc gtgccagctg cattaatgaa tcggccaacg cgcggggaga ggcggtttgc    4380
gtattgggcg ctcttccgct tcctcgctca ctgactcgct gcgctcggtc gttcggctgc    4440
ggcgagcggt atcagctcac tcaaaggcgg taatacggtt atccacagaa tcagggggata    4500
acgcaggaaa gaacatgtga gcaaaaggcc agcaaaaggc caggaaccgt aaaaaggccg    4560
cgttgctggc gttttcccat aggctccgcc ccctgacga gcatcacaaa aatcgacgct    4620
caagtcagag gtggcgaaac ccgacaggac tataaagata ccaggcgttt ccccctggaa    4680
gctccctcgt gcgctctcct gttccgaccc tgccgcttac cggatacctg tccgcctttc    4740
tcccttcggg aagcgtggcg ctttctcata gctcacgctg taggtatctc agttcggtgt    4800
aggtcgttcg ctccaagctg ggctgtgtgc acgaaccccc cgttcagccc gaccgctgcg    4860
ccttatccgg taactatcgt cttgagtcca acccggtaag acacgactta tcgccactgg    4920
cagcagccac tggtaacagg attagcagag cgaggtatgt aggcggtgct acagagttct    4980
tgaagtggtg gcctaactac ggctacacta aaggacagt attggtatc tgcgctctgc    5040
tgaagccagt taccttcgga aaaagagttg gtagctcttg atccggcaaa caaaccaccg    5100
ctggtagcgg tggttttttt gtttgcaagc agcagattac gcgcagaaaa aaaggatctc    5160
aagaagatcc tttgatcttt tctacggggt ctgacgctca gtggaacgaa aactcacgtt    5220
aagggatttt ggtcatgaga ttatcaaaaa ggatcttcac ctagatcctt ttaaattaaa    5280
aatgaagttt taaatcaatc taaagtatat atgagtaaac ttggtctgac agttaccaat    5340
```

-continued

```
gcttaatcag tgaggcacct atctcagcga tctgtctatt tcgttcatcc atagttgcct    5400
gactccccgt cgtgtagata actacgatac gggagggctt accatctggc cccagtgctg    5460
caatgatacc gcgagaccca cgctcaccgg ctccagattt atcagcaata aaccagccag    5520
ccggaagggc cgagcgcaga agtggtcctg caactttatc cgcctccatc cagtctatta    5580
attgttgccg ggaagctaga gtaagtagtt cgccagttaa tagtttgcgc aacgttgttg    5640
ccattgctac aggcatcgtg gtgtcacgct cgtcgtttgg tatggcttca ttcagctccg    5700
gttcccaacg atcaaggcga gttacatgat cccccatgtt gtgcaaaaaa gcggttagct    5760
ccttcggtcc tccgatcgtt gtcagaagta agttggccgc agtgttatca ctcatggtta    5820
tggcagcact gcataattct cttactgtca tgccatccgt aagatgcttt tctgtgactg    5880
gtgagtactc aaccaagtca ttctgagaat agtgtatgcg cgaccgagt tgctcttgcc    5940 cggcgtcaat acgggataat accgcgccac atagcagaac tttaaaagtg ctcatcattg    6000
gaaaacgttc ttcggggcga aaactctcaa ggatcttacc gctgttgaga tccagttcga    6060
tgtaacccac tcgtgcaccc aactgatctt cagcatcttt tactttcacc agcgtttctg    6120
ggtgagcaaa aacaggaagg caaaatgccg caaaaaaggg aataagggcg acacggaaat    6180
gttgaatact catactcttc ctttttcaat attattgaag catttatcag ggttattgtc    6240
tcatgagcgg atacatattt gaatgtattt agaaaaataa acaaataggg gttccgcgca    6300
catttccccg aaaagtgcca cctgacgtct aagaaaccat tattatcatg acattaacct    6360
ataaaaatag gcgtatcacg aggccctttc gtc                                 6393
```

<210> SEQ ID NO 8
<211> LENGTH: 42
<212> TYPE: DNA
<213> ORGANISM: Artificial Sequence
<220> FEATURE:
<223> OTHER INFORMATION: PCR primer, gen-f1

<400> SEQUENCE: 8

```
attatttcta gaaggacaga aatgcctcga cttcgctgct gc                       42
```

<210> SEQ ID NO 9
<211> LENGTH: 45
<212> TYPE: DNA
<213> ORGANISM: Artificial Sequence
<220> FEATURE:
<223> OTHER INFORMATION: PCR primer, gen-r1

<400> SEQUENCE: 9

```
attatttcta gattaggtgg cggtacttgg gtcgatatca aagtg                    45
```

<210> SEQ ID NO 10
<211> LENGTH: 7233
<212> TYPE: DNA
<213> ORGANISM: Artificial Sequence
<220> FEATURE:
<223> OTHER INFORMATION: PHA depolymerase gene-targeting vector, pPZ1

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accataatcg gcattttctt ttgcgttttt atttgttaac tgttaattgt ccttgttcaa    240
ggatgctgtc tttgacaaca gatgtttttct tgcctttgat gttcagcagg aagctaggcg    300
```

-continued

| | |
|---|---|
| caaacgttga ttgtttgtct gcgtagaatc ctctgtttgt catatagctt gtaatcacga | 360 |
| cattgttcc tttcgcttga ggtacagcga agtgtgagta agtaaaggtt acatcgttag | 420 |
| gatcaagatc cattttaac acaaggccag ttttgttcag cggcttgtat gggccagtta | 480 |
| aagaattaga aacataacca agcatgtaaa tatcgttaga cgtaatgccg tcaatcgtca | 540 |
| ttttgatcc gcgggagtca gtgaacagat accatttgcc gttcatttta aagacgttcg | 600 |
| cgcgttcaat tcatctgtt actgtgttag atgcaatcag cggtttcatc acttttttca | 660 |
| gtgtgtaatc atcgtttagc tcaatcatac cgagagcgcc gtttgctaac tcagccgtgc | 720 |
| gttttttatc gctttgcaga agttttgac tttcttgacg gaagaatgat gtgcttttgc | 780 |
| catagtatgc tttgttaaat aaagattctt cgccttggta gccatcttca gttccagtgt | 840 |
| ttgcttcaaa tactaagtat ttgtggcctt tatcttctac gtagtgagga tctctcagcg | 900 |
| tatggttgtc gcctgagctg tagttgcctt catcgatgaa ctgctgtaca ttttgatacg | 960 |
| tttttccgtc accgtcaaag attgatttat aatcctctac accgttgatg ttcaaagagc | 1020 |
| tgtctgatgc tgatacgtta acttgtgcag ttgtcagtgt ttgtttgccg taatgtttac | 1080 |
| cggagaaatc agtgtagaat aaacggatt ttccgtcaga tgtaaatgtg gctgaacctg | 1140 |
| accattcttg tgtttggtct tttaggatag aatcatttgc atcgaatttg tcgctgtctt | 1200 |
| taaagacgcg gccagcgttt ttccagctgt caatagaagt ttcgccgact ttttgataga | 1260 |
| acatgtaaat cgatgtgtca tccgcatttt taggatctcc ggctaatgca aagacgatgt | 1320 |
| ggtagccgtg atagtttgcg acagtgccgt cagcgttttg taatggccag ctgtcccaaa | 1380 |
| cgtccaggcc ttttgcagaa gagatatttt taattgtgga cgaatcgaac tcaggaactt | 1440 |
| gatattttc atttttttgc tgttcaggga tttgcagcat atcatggcgt gtaatatggg | 1500 |
| aaatgccgta tgtttcctta tatggctttt ggttcgtttc tttcgcaaac gcttgagttg | 1560 |
| cgcctcctgc cagcagtgcg gtagtaaagg ttaatactgt tgcttgtttt gcaaactttt | 1620 |
| tgatgttcat cgttcatgtc tccttttta tgtactgtgt tagcggtctg cttcttccag | 1680 |
| ccctcctgtt tgaagatggc aagttagtta cgcacaataa aaaagacct aaatatgta | 1740 |
| aggggtgacg ccaaagtata cactttgccc tttacacatt ttaggtcttg cctgctttat | 1800 |
| cagtaacaaa cccgcgcgat ttacttttcg acctcattct attagactct cgtttggatt | 1860 |
| gcaactggtc tattttcctc ttttgtttga tagaaaatca taaaaggatt tgcagactac | 1920 |
| gggcctaaag aactaaaaaa tctatctgtt tcttttcatt ctctgtattt tttatagttt | 1980 |
| ctgttgcatg ggcataaagt tgccttttta atcacaattc agaaaatatc ataatatctc | 2040 |
| attcactaa ataatagtga acggcaggta tatgtgatgg gttaaaaagg atcgatcctc | 2100 |
| tagctagagt cgatcttcgc cagcagggcg aggatcgtgg catcaccgaa ccgcgccgtg | 2160 |
| cgcgggtcgt cggtgagcca gagtttcagc aggccgccca gcggcccag tcgccattg | 2220 |
| atgcgggcca gctcgcggac gtgctcatag tccacgacgc ccgtgatttt gtagccctgg | 2280 |
| ccgacggcca gcaggtaggc cgacaggctc atgccggccg ccgccgcctt tcctcaatc | 2340 |
| gctcttcgtt cgtctggaag gcagtacacc ttgataggtg ggctgccctt cctggttggc | 2400 |
| ttggttcat cagccatccg cttgccctca tctgttacgc cggcggtagc cggccagcct | 2460 |
| cgcagagcag gattcccgtt gagcaccgcc aggtgcgaat aagggacagt gaagaaggaa | 2520 |
| cacccgctcg cgggtgggcc tacttcacct atcctgcccg gctgacgccg ttggatacac | 2580 |
| caaggaaagt ctacacgaac cctttggcaa atcctgtat atcgtgcgaa aaaggatgga | 2640 |

```
tataccgaaa aaatcgctat aatgaccccg aagcagggtt atgcagcgga aaagcgctgc   2700
ttccctgctg ttttgtggaa tatctaccga ctggaaacag gcaaatgcag gaaattactg   2760
aactgagggg acaggcgaga gacgatgcca aagagctaca ccgacgagct ggccgagtgg   2820
gttgaatccc gcgcggccaa gaagcgccgg cgtgatgagg ctgcggttgc gttcctggcg   2880
gtgagggcgg atgtcgatat gcgtaaggag aaaataccgc atcaggcgca tgcatatttg   2940
aatgtattta gaaaaataaa caaaaagagt ttgtagaaac gcaaaaaggc catccgtcag   3000
gatggccttc tgcttaattt gatgcctggc agtttatggc gggcgtcctg cccgccaccc   3060
tccgggccgt tgcttcgcaa cgttcaaatc cgctcccggc ggatttgtcc tactcaggag   3120
agcgttcacc gacaaacaac agataaaacg aaaggcccag tctttcgact gagcctttcg   3180
ttttatttga tgcctggcag ttccctactc tcgcatgggg agaccccaca ctaccatcgg   3240
cgctacggcg tttcacttct gagttcggca tggggtcagg tgggaccacc gcgctactgc   3300
cgccaggcaa attctgtttt atcagaccgc ttctgcgttc tgatttaatc tgtatcaggc   3360
tgaaaatctt ctctcatccg ccaaaacagc caagctcgcc attcgccatt caggctgcgc   3420
aactgttggg aagggcgatc ggtgcgggcc tcttcgctat tacgccagct ggcgaaaggg   3480
ggatccgcca ggccagcaag cgcatgttga ccaacggaat caagggtcg tcgtcgccgg   3540 ccaggaccag ggtcggctga ttgatcttgt gcagccagtg gatgctggtc cagccgaagc   3600
cggcgaacag ttgccagtag taaccgagct tgcccgccga acggaccttt gccgcatggc   3660
ttgcagccag cgtcgggtcg cgacggaacg agccgccgta gatcatcggc gcaatgcgga   3720
tcacgtggga tggctggatg taccgtcgtg ggctggccat catccacaag actttcggct   3780
tgcccggcac catcaccgta cccgcggctg tcgctgccag gaccagcttc ttgcaccgct   3840
ctagattagg tggcggtact tgggtcgata tcaaagtgca tcacttcttc ccgtatgccc   3900
aactttgtat agagagccac tgcgggatcg tcaccgtaat ctgcttgcac gtagatcaca   3960
taagcaccaa gcgcgttggc ctcatgcttg aggagattga tgagcgcggt ggcaatgccc   4020
tgcctccggt gctcgccgga gactgcgaga tcatagatat agatctcact acgcggctgc   4080
tcaaacctgg gcagaacgta agccgcgaga gcgccaacaa ccgcttcttg gtcgaaggca   4140
gcaagcgcga tgaatgtctt actacggagc aagttcccga ggtaatcgga gtccggctga   4200
tgttgggagt aggtggctac gtctccgaac tcacgaccga aaagatcaag agcagcccgc   4260
atggatttga cttggtcagg gccgagccta catgtgcgaa tgatgcccat acttgagcca   4320
cctaactttg ttttagggcg actgccctgc tgcgtaacat cgttgctgct gcgtaacatc   4380
gttgctgctc cataacatca acatcgacc cacggcgtaa cgcgcttgct gcttggatgc   4440
ccgaggcata gactgtacaa aaaaacagtc ataacaagcc atgaaaaccg ccactgcgcc   4500
gttaccaccg ctgcgttcgg tcaaggttct ggaccagttg cgtgagcgca tacgctactt   4560
gcattacagt ttacgaaccg aacaggctta tgtcaactgg ttcgtgcct tcatccgttt   4620 ccacggtgtg cgtcacccgg caaccttggg cagcagcgaa gtcgaggcat ttctgtcctt   4680
ctagatagtc ataggcgaac tgttgcgcaa gggcgccacc ccatgacacg ccgatcacgt   4740
tgactcgccc gtaatcgagg tagtcgagca tgcgtgccgt gagctttgcc aggcctggga   4800
aacgatatgg acgattgggc gtcgatgaac cgccaacacc gggtacgtcg aaggcgatga   4860
cttcgaggtc cgggtccagc gctgcgacga acggaaacac cagctccagg ttggcgccga   4920
tgccgttgaa aatcagcaag ggcgtcaagt gaggcttgcc ggggcgcacc gccgtgcgga   4980
gggtctggcc atcgagctcg gcgtaatcat ggtcatagct gtttcctgtg tgaaattgtt   5040
```

-continued

```
atccgctcac aattccacac aacatacgag ccggaagcat aaagtgtaaa gcctggggtg      5100
cctaatgagt gagctaactc acattaattg cgttgcgctc actgcccgct ttccagtcgg      5160
gaaacctgtc gtgccagctg cattaatgaa tcggccaacg cgcggggaga ggcggtttgc      5220
gtattgggcg ctcttccgct tcctcgctca ctgactcgct gcgctcggtc gttcggctgc      5280
ggcgagcggt atcagctcac tcaaaggcgg taatacggtt atccacagaa tcaggggata      5340
acgcaggaaa gaacatgtga gcaaaaggcc agcaaaaggc caggaaccgt aaaaaggccg      5400
cgttgctggc gtttttccat aggctccgcc cccctgacga gcatcacaaa aatcgacgct      5460
caagtcagag gtggcgaaac ccgacaggac tataaagata ccaggcgttt ccccctggaa      5520
gctccctcgt gcgctctcct gttccgaccc tgccgcttac cggatacctg tccgcctttc      5580
tcccttcggg aagcgtggcg ctttctcata gctcacgctg taggtatctc agttcggtgt      5640
aggtcgttcg ctccaagctg gctgtgtgc acgaaccccc cgttcagccc gaccgctgcg      5700
ccttatccgg taactatcgt cttgagtcca acccggtaag acacgactta tcgccactgg      5760
cagcagccac tggtaacagg attagcagag cgaggtatgt aggcggtgct acagagttct      5820
tgaagtggtg gcctaactac ggctacacta aaggacagt atttggtatc tgcgctctgc      5880
tgaagccagt taccttcgga aaagagttg gtagctcttg atccggcaaa caaaccaccg      5940
ctggtagcgg tggtttttt gtttgcaagc agcagattac gcgcagaaaa aaaggatctc      6000
aagaagatcc tttgatcttt tctacggggt ctgacgctca gtggaacgaa aactcacgtt      6060
aagggatttt ggtcatgaga ttatcaaaaa ggatcttcac ctagatcctt ttaaattaaa      6120
aatgaagttt taaatcaatc taagtatat atgagtaaac ttggtctgac agttaccaat      6180
gcttaatcag tgaggcacct atctcagcga tctgtctatt tcgttcatcc atagttgcct      6240
gactccccgt cgtgtagata actacgatac gggagggctt accatctggc cccagtgctg      6300
caatgatacc gcgagaccca cgctcaccgg ctccagattt atcagcaata aaccagccag      6360
ccggaagggc cgagcgcaga agtggtcctg caactttatc cgcctccatc cagtctatta      6420
attgttgccg ggaagctaga gtaagtagtt cgccagttaa tagtttgcgc aacgttgttg      6480
ccattgctac aggcatcgtg gtgtcacgct cgtcgtttgg tatggcttca ttcagctccg      6540
gttcccaacg atcaaggcga gttacatgat cccccatgtt gtgcaaaaaa gcggttagct      6600
ccttcggtcc tccgatcgtt gtcagaagta agttggccgc agtgttatca ctcatggtta      6660
tggcagcact gcataattct cttactgtca tgccatccgt aagatgcttt tctgtgactg      6720
gtgagtactc aaccaagtca ttctgagaat agtgtatgcg gcgaccgagt tgctcttgcc      6780
cggcgtcaat acgggataat accgcgccac atagcagaac tttaaaagtg ctcatcattg      6840
gaaaacgttc ttcgggcga aaactctcaa ggatcttacc gctgttgaga tccagttcga      6900
tgtaacccac tcgtgcaccc aactgatctt cagcatcttt tactttcacc agcgtttctg      6960
ggtgagcaaa aacaggaagg caaaatgccg caaaaaaggg aataagggcg acacggaaat      7020
gttgaatact catactcttc ctttttcaat attattgaag catttatcag ggttattgtc      7080
tcatgagcgg atacatattt gaatgtattt agaaaaataa acaaataggg gttccgcgca      7140
catttccccg aaaagtgcca cctgacgtct aagaaaccat tattatcatg acattaacct      7200
ataaaaatag gcgtatcacg aggccctttc gtc                                  7233
```

<210> SEQ ID NO 11
<211> LENGTH: 640
<212> TYPE: DNA

<213> ORGANISM: Artificial Sequence
<220> FEATURE:
<223> OTHER INFORMATION: partial sequence for PHA depolymerase
      gene-targeting

<400> SEQUENCE: 11

```
ttgctgattt tcaacggcat cggcgccaac ctggagctgg tgtttccgtt cgtcgcagcg      60
ctggacccgg acctcgaagt catcgccttc gacgtacccg tgttggcggt tcatcgacg      120
cccaatcgtc catatcgttt cccaggcctg gcaaagctca cggcacgcat gctcgactac     180
ctcgattacg ggcgagtcaa cgtgatcggc gtgtcatggg gtggcgccct tgcgcaacag     240
ttcgcctatg actatccaga gcggtgcaag aagctggtcc tggcagcgac agccgcgggt     300
acggtgatgg tgccgggcaa gccgaaagtc ttgtggatga tggccagccc acgacggtac     360
atccagccat cccacgtgat ccgcattgcg ccgatgatct acggcggctc gttccgtcgc     420
gacccgacgc tggctgcaag ccatgcggca aggtccgtt cggcgggcaa gctcggttac      480
tactggcaac tgttcgccgg cttcggctgg accagcatcc actggctgca caagatcaat    540
cagccgaccc tggtcctggc cggcgacgac gaccccttga ttccgttggt caacatgcgc    600
ttgctggcct ggcggatccc caatgcccaa ctgcacatca                          640
```

<210> SEQ ID NO 12
<211> LENGTH: 517
<212> TYPE: DNA
<213> ORGANISM: Artificial Sequence
<220> FEATURE:
<223> OTHER INFORMATION: partial sequence for PHA depolymerase
      gene-targeting

<400> SEQUENCE: 12

```
cctcgaagtc atcgccttcg acgtacccgg tgttggcggt tcatcgacgc ccaatcgtcc      60
atatcgtttc ccaggcctgg caaagctcac ggcacgcatg ctcgactacc tcgattacgg     120
gcgagtcaac gtgatcggcg tgtcatgggg tggcgcccct tgcgcaacagt tcgcctatga    180
ctatccagag cggtgcaaga agctggtcct ggcagcgaca gccgcgggta cggtgatggt    240
gccgggcaag ccgaaagtct tgtggatgat ggccagccca cgacggtaca tccagccatc    300
ccacgtgatc cgcattgcgc cgatgatcta cggcggctcg ttccgtcgcg acccgacgct    360
ggctgcaagc catgcggcaa aggtccgttc ggcgggcaag ctcggttact actggcaact    420
gttcgccggc ttcggctgga ccagcatcca ctggctgcac aagatcaatc agccgaccct    480
ggtcctggcc ggcgacgacg acccctttgat tccgttg                             517
```

<210> SEQ ID NO 13
<211> LENGTH: 161
<212> TYPE: DNA
<213> ORGANISM: Artificial Sequence
<220> FEATURE:
<223> OTHER INFORMATION: partial sequence for PHA depolymerase
      gene-targeting

<400> SEQUENCE: 13

```
gtgtcatggg gtggcgccct tgcgcaacag ttcgcctatg actatccaga gcggtgcaag      60
aagctggtcc tggcagcgac agccgcgggt acggtgatgg tgccgggcaa gccgaaagtc     120
ttgtggatga tggccagccc acgacggtac atccagccat c                         161
```

<210> SEQ ID NO 14
<211> LENGTH: 450
<212> TYPE: DNA

<210> SEQ ID NO 14
<211> LENGTH: 450
<212> TYPE: DNA
<213> ORGANISM: Artificial Sequence
<220> FEATURE:
<223> OTHER INFORMATION: partial sequence for PHA depolymerase
      gene-targeting

<400> SEQUENCE: 14

```
gacctggatg gccagaccct ccgcacggcg gtgcgccccg gcaagcctca cttgacgccc      60
ttgctgattt tcaacggcat cggcgccaac ctggagctgg tgtttccgtt cgtcgcagcg     120
ctggacccgg acctcgaagt catcgccttc gacgtacccg gtgttggcgg ttcatcgacg     180
cccaatcgtc catatcgttt cccaggcctg gcaaagctca cggcacgcat tggctgcaag     240
ccatgcggca aggtccgtt cggcgggcaa gctcggttac tactggcaac tgttcgccgg      300
cttcggctgg accagcatcc actggctgca caagatcaat cagccgaccc tggtcctggc     360
cggcgacgac gacccttga ttccgttggt caacatgcgc ttgctggcct ggcggatccc      420
caatgcccaa ctgcacatca tcgacgacgg                                      450
```

<210> SEQ ID NO 15
<211> LENGTH: 278
<212> TYPE: DNA
<213> ORGANISM: Artificial Sequence
<220> FEATURE:
<223> OTHER INFORMATION: partial sequence for PHA depolymerase
      gene-targeting

<400> SEQUENCE: 15

```
tgctgatttt caacggcatc ggcgccaacc tggagctggt gtttccgttc gtcgcagcgc      60
tggacccgga cctcgaagtc atcgccttcg acgtacccgg tgttggcggt tcatcgacgc     120
ccaatcgtca ggtccgttc ggcgggcaag ctcggttact actggcaact gttcgccggc      180
ttcggctgga ccagcatcca ctggctgcac aagatcaatc agccgaccct ggtcctggcc     240
ggcgacgacg acccttgat tccgttggtc aacatgcg                              278
```

BACTERIUM FOR PRODUCING POLYHYDROXYALKANOATE HAVING POLYHYDROXYALKANOATE DEPOLYMERASE GENE DISRUPTED AND METHOD FOR PRODUCING POLYHYDROXYALKANOATE USING THE SAME

BACKGROUND OF THE INVENTION

1. Field of the Invention

The present invention is related to a bacterium for producing polyhydroxyalkanoate in which the gene coding for polyhydroxyalkanoate depolymerase is disrupted and to a method for producing polyhydroxyalkanoate using the same. Also related is a gene targeting vector to disrupt the gene coding for the polyhydroxyalkanoate depolymerase of the bacterium for producing polyhydroxyalkanoate and a method for disrupting the same.

2. Related Background Art

Until now, it has been reported that many microbes produce and accumulate in the body poly-3-hydroxy butyrate (PHB) or other poly-3-hydroxyalkanoate (PHA) ("Biodegradable plastic handbook", edited by the biodegradable plastic study group, NTS Inc. P178-197 (1995)). These polymers, like conventional plastics, can be used for producing various products by melt processing and the like. Furthermore, these polymers have an advantage of being completely degraded by microbes in the nature and do not cause pollution by remaining in the natural environment, unlike many conventional synthetic polymers, because they are biodegradable. They are also superior in biocompatibility, and would be expected to have applications as soft material for medical use and the like.

Recently in particular, it is expected that unusual PHA in which substituents other than alkyl group are introduced in the side chain would be very useful considering expanding application of microbially produced PHA, for example an application as a functional polymer. Examples of such substituents include groups containing an aromatic ring (phenyl group, phenoxy group, benzoyl group and the like), unsaturated hydrocarbons, ester group, aryl group, cyano group, halogenated hydrocarbons, epoxides, thioethers and the like.

It has been known that microbially produced PHA can have various compositions and structures depending upon the relevant microbial species, the composition of the medium, the culture condition and the like. Various researches have been carried out on such PHA producing microbes, and the biosynthetic pathway of PHA has been relatively well investigated.

Up until now, polyhydroxyalkanoate synthases are classified into three classes by substrate specificity and subunit composition.

Polyhydroxyalkanoate synthases belonging to "the first class" are found in Ralstonia eutropha, Aeromonas punctata and the like which use, as substrate, thioesters of short-chain-length 3-hydroxyalkanoates with C3-C5 carbons with a coenzyme CoA.

Polyhydroxyalkanoate synthases belonging to "the second class" are found in *Pseudomonas oleovorans* and *Pseudomonas aeruginosa* which use, as substrate, thioesters of various "unusual" 3-hydroxyalkanoates as well as medium-chain-length 3-hydroxyalkanoates with C6-C14 carbons with the coenzyme CoA.

In both the first and second classes, polyhydroxyalkanoate synthases are composed of a single subunit of molecular weight 61-73 kDa.

Polyhydroxyalkanoate synthases belonging to "the third class" are found in *Allochromatium vinosum* and *Ectothiorhodospira shaposhnikovii* and composed of two different subunits of about 40 kDA. They have a substrate specificity similar to that of the first class polyhydroxyalkanoate syntheses and use thioesters of short-chain-length 3-hydroxyalkanoates with 3-5 carbons with the coenzyme CoA.

On the other hand, there remains much to be done for the degradation pathway of PHA. The Journal of Biological Chemistry 266, 2191 (1991) has disclosed that by treating *Pseudomonas oleovorans* containing the polyhydroxyalkanoate synthase with the substrate specificity of the "second class" with a chemical mutagen, a mutant strain was obtained which were not able to degrade intracellular PHA and that using this mutant, a gene which complements PHA degrading activity was cloned. According to this paper, the PHA synthase gene (phaC1, phaC2) and the PHA depolymerase (phaZ) gene formed a cluster and assumed an arrangement of phaC1-phaZ-phaC2. Since then, it has been discovered that in other bacteria such as *Pseudomonas aeruginosa, Pseudomonas* sp. 61-3, *Pseudomonas resinovolans, Pseudomonas putida, Pseudomonas mendocina* and the like, which contains polyhydroxyalkanoate synthase with the substrate specificity of the second class, the genes are arranged as phaC1-phaZ-phaC2.

Although mutants, in which the PHA depolymerase gene do not function, have been isolated in the process of these studies, the relationship between the PHA depolymerase activity and the amount of PHA accumulated in the cells is not known.

On the other hand, in Japanese Patent Application Laid-Open No. H11-113574, what is shown is depolymerase of poly-3-hydroxy butyrate (PHB), which is isolated from *Alcaligenes eutrophas* containing polyhydroxyalkanoate synthase that belongs to "the first class". Further, in Japanese Patent Application Laid-Open No. H9-191887, what is shown is depolymerase of poly-3-hydroxy butyrate (PHB), which is isolated from *Alcaligenes faecalis* containing polyhydroxyalkanoate synthase that belongs to "the first class". Still further, in Japanese Patent Application Laid-Open No. H6-086681, what is shown is depolymerase of poly-3-hydroxy butyrate (PHB), which is isolated from *Zoogolea ramigera* containing polyhydroxyalkanoate synthase that belongs to "the first class".

Patent Document 1: Japanese Patent Application Laid-Open No. H11-113574

Patent Document 2: Japanese Patent Application Laid-Open No. H9-191887

Patent Document 3: Japanese Patent Application Laid-Open No. H6-086681

Non-patent Document 1: "Biodegradable plastic handbook", edited by the biodegradable plastic study group, NTS Inc. P178-197 (1995)

Non-patent Document 2: The Journal of Biological Chemistry 266, 2191 (1991)

SUMMARY OF THE INVENTION

To obtain PHA, which is expected to be a functional polymer, cheaply, and in large quantity stably, it is necessary to improve the productivity. For this purpose, it is believed to be important not only to improve the efficiency of the biosynthesis by the microbe but also to suppress the degradation. Since depolymerase of poly-3-hydroxy butyrate (PHB), isolated from the microbe containing polyhydroxyalkanoate synthase that belongs to the first class, is involved in degradation of PHA which is composed of 3-hydroxyalkanate units with short chains of 3 to 5 carbons, it can not be utilized to obtain PHA expected to be functional polymer (especially unusual PHA), cheaply and in large quantity stably. The first objective of the present invention is to provide an isogenic strain line of unusual PHA producing microbe with improved productivity by carrying out gene disruption on the polyhydroxyalkanoate depolymerase gene of the microbe containing polyhydroxyalkanoate synthase that belongs to the second class.

The general method for obtaining such a strain is to carry out screening the pool of randomly mutated bacteria, which requires tedious experimental manipulations, and thus a simpler method is desired to obtain an unusual PHA producing microbe in which the polyhydroxyalkanoate depolymerase gene is disrupted. The second objective of the present invention is to provide a simple method for obtaining an unusual PHA producing microbe in which the polyhydroxyalkanoate depolymerase gene is disrupted.

The present inventors, having studied hard, have isolated the PHA depolymerase gene from *Pseudomonas* sp. YN21 line that is one of the unusual PHA producing microbes and have constructed a vector targeting the polyhydroxyalkanoate depolymerase gene using the base sequence of the gene. By using the constructed gene targeting vector, a bacterial strain has been crated which is isogenic strain with the *Pseudomonas* sp. YN21 strain, one of the unusual PHA producing microbes and has the gene coding for the polyhydroxyalkanoate depolymerase disputed. Further, it has been discovered that the gene of the polyhydroxyalkanoate depolymerase of the other polyhydroxyalkanoate producing microbes that contain polyhydroxyalkanoate synthase of the second class may be disrupted specifically by using the constructed gene targeting vector. Still further, to complete the present invention, it has been discovered that by using the created bacterial strain, in which the gene coding for polyhydroxyalkanoate depolymerase is disrupted, there is an increased productivity of PHA which is composed of not only medium-chain-length 3-hydroxyalkanates with C6-C14 carbons but also various "unusual" 3-hydrodyalkanoates.

According to the first aspect of the present invention, there is provided a bacterium for producing polyhydroxyalkanoate, in which a gene coding for the polyhydroxyalkanoate depolymerase is disrupted.

According to the second aspect of the present invention, there is provided *Pseudomonas* sp. PZ1 strain (FERM BP-08571) as a bacterium for producing polyhydroxyalkanoate, wherein the PZ1 strain is isogenic strain to a bacterium for producing polyhyrdoxyalkanoate, *Pseudomonas* sp. YN21 strain (FERM BP-08569) and a gene coding for the polyhydroxyalkanoate depolymerase of the PZ1 strain is disrupted.

According to the third aspect of the present invention, there is provided a method for producing a polyhydroxyalkanoate comprising the steps of: culturing a bacterium for producing polyhydroxyalkanoate, in which a gene coding for polyhydroxyalkanoate depolymerase is disrupted; and recovering the polyhydroxyalkanoate from the culture medium.

According to the fourth aspect of the present invention, there is provided a targeting vector for a polyhydroxyalkanoate depolymerase gene, comprising (1) a DNA for homologous recombination selected from the group consisting of (a) a DNA containing the base sequence shown in SEQ ID NO:1 or a portion thereof and (b) a DNA hybridizing under stringent conditions with a DNA which is complementary to the DNA containing the base sequence shown in SEQ ID NO:1, or a portion thereof, (2) a portion for disrupting a polyhydroxyalkanoate depolymerase gene, and (3) a vector, wherein these materials of the above items (1) to (3) are operably linked.

According to a further aspect of the present invention, there is provided a host cell transformed by the targeting vector according to the fourth aspect of the present invention. According to a further aspect of the present invention, there is provided a method for producing an isogenic strain of a bacterium for producing polyhydroxyalkanoate in which the gene coding for the polyhydroxyalkanoate depolymerase is disrupted, wherein a homologous recombination of the polyhydroxyalkanoate depolymerase gene on the chromosomal DNA of the bacterium for producing polyhydroxyalkanoate, the homologous recombination being caused by conjugation between the just above-mentioned host cell and the bacterium for producing polyhydroxyalkanoate so that the gene coding for the polyhydroxyalkanoate depolymerase is disrupted.

According to a further aspect of the present invention, there is provided a method for producing an isogenic strain of a bacterium for producing polyhydroxyalkanoate in which the gene coding for the polyhydroxyalkanoate depolymerase is disrupted, wherein the gene coding for the polyhydroxyalkanoate depolymerase is disrupted by homologous recombination between a DNA coding for the targeting vector according to the fourth aspect of the present invention and the polyhydroxyalkanoate depolymerase gene on the chromosomal DNA of the bacterium for producing polyhydroxyalkanoate.

According to the fifth aspect of the present invention, there is provided a targeting vector for a polyhydroxyalkanoate depolymerase gene directed to a bacterium for producing polyhydroxyalkanoate, comprising:

(1) a DNA selected from the group consisting of (a) a DNA containing the base sequence shown in SEQ ID NO:1 or a portion thereof, and (b) a DNA hybridizing under stringent conditions with a DNA which is complementary to the DNA containing the base sequence shown in SEQ ID NO:1, or a portion thereof, (2) a foreign DNA, (3) a replication gene incompatible with the replication gene of the bacterium for producing polyhydroxyalkanoate, (4) an conjugative transfer origin gene, and (5) a vector, wherein these materials of the above items (1) to (5) are operably linked.

The targeting vector for a polyhydroxyalkanoate depolymerase gene according to the fifth aspect of the present invention, wherein the foreign DNA is a gentamicin resistant gene or a kanamycin resistant gene.

According to a further aspect of the present invention, there is provided a host cell transformed by the targeting vector according to the fifth aspect of the present invention.

According to a further aspect of the present invention, there is provided a method for producing an isogenic strain of a bacterium for producing polyhydroxyalkanoate in which the gene coding for the polyhydroxyalkanoate depolymerase is disrupted, wherein a homologous recombination of the polyhydroxyalkanoate depolymerase gene on the chromosomal DNA of the bacterium for producing polyhydroxyalkanoate, the homologous recombination being caused by conjugation between the just above-mentioned host cell and the bacterium for producing polyhydroxyalkanoate so that the gene coding for the polyhydroxyalkanoate depolymerase is disrupted.

According to the sixth aspect of the present invention, there is provided a targeting vector for a polyhydroxyalkanoate depolymerase gene directed to a bacterium for producing polyhydroxyalkanoate, comprising:

(1) a DNA selected from the group consisting of (a) a DNA containing the base sequence shown in SEQ ID NO:1 or a portion thereof, and (b) a DNA hybridizing under stringent conditions with a DNA which is complementary to the DNA containing the base sequence shown in SEQ ID NO:1, or a portion thereof, (2) another DNA defined by the above item (1), or a foreign DNA inserted into a portion of the other DNA, (3) a replication gene incompatible with a replication gene of the bacterium for producing polyhydroxyalkanoate, (4) a susceptibility gene, (5) an conjugative transfer origin gene, and (6) a vector, wherein these materials of the above items (1) to (6) are operably linked. The susceptibility gene is preferably a Levansucrase gene. The foreign DNA is preferably a gentamicin resistant gene or a kanamycin resistant gene.

According to a further aspect of the present invention, there is provided a host cell transformed by the targeting vector according to the sixth aspect of the present invention. According to a further aspect of the present invention, there is provided a method for producing an isogenic strain of a bacterium for producing polyhydroxyalkanoate in which the gene coding for the polyhydroxyalkanoate depolymerase is disrupted, wherein a homologous recombination of the polyhydroxyalkanoate depolymerase gene on the chromosomal DNA of the bacterium for producing polyhydroxyalkanoate, the homologous recombination being caused by conjugation between the just above-mentioned host cell and the bacterium for producing polyhydroxyalkanoate so that the gene coding for the polyhydroxyalkanoate depolymerase is disrupted.

It is believed that in the bacterium for producing polyhydroxyalkanoate of the present invention, in which the gene coding for polyhydroxyalkanoate depolymerase is disrupted, the productivity of PHA is improved compared to a normal producer because synthesized PHA is not degraded due to polyhydroxyalkanoate depolymerase being disrupted. The bacterium for producing polyhydroxyalkanoate, *Pseudomonas* sp. YN21 strain (FERM BP-08569), was isolated by the present inventors and can synthesize various unusual PHA. Thus, using polyhydroxyalkanoate producing *Pseudomonas* sp. PZ1 strain (FERM BP-08571), which is an isogenic strain line of YN21 strain and in which the gene coding for polyhydroxyalkanoate depolymerase is disrupted, unusual PHA can be produced with a higher productivity than before.

Further, the method of the present invention for producing polyhydroxyalkanoate includes a step of culturing the bacterium for producing polyhydroxyalkanoate, in which the gene coding for polyhydroxyalkanoate depolymerase is disrupted, and a step of recovering polyhydroxyalkanoate from the culture medium, and PHA can be produced with a higher productivity using the microbial producer having higher production capability than before.

Still further, the vector targeting the polyhydroxyalkanoate depolymerase gene of the present invention can disrupt efficiently the polyhydroxyalkanoate depolymerase gene of the bacterium for producing polyhydroxyalkanoate containing a polyhydroxyalkanoate synthase that belongs to the second class.

Yet still further, the method of the present invention for producing the isogenic strain line of the bacterium for producing polyhydroxyalkanoate, in which the gene coding for the polyhydroxyalkanoate depolymerase is disrupted, can disrupt the gene coding for polyhydroxyalkanoate depolymerase expediently by homologous recombination of the aforementioned gene targeting vector DNA of the present invention with the polyhydroxyalkanoate depolymerase gene on the chromosomal DNA of the bacterium for producing polyhydroxyalkanoate.

BRIEF DESCRIPTION OF THE SEVERAL VIEWS OF DRAWING

DETAILED DESCRIPTION OF THE INVENTION

Figure 1:
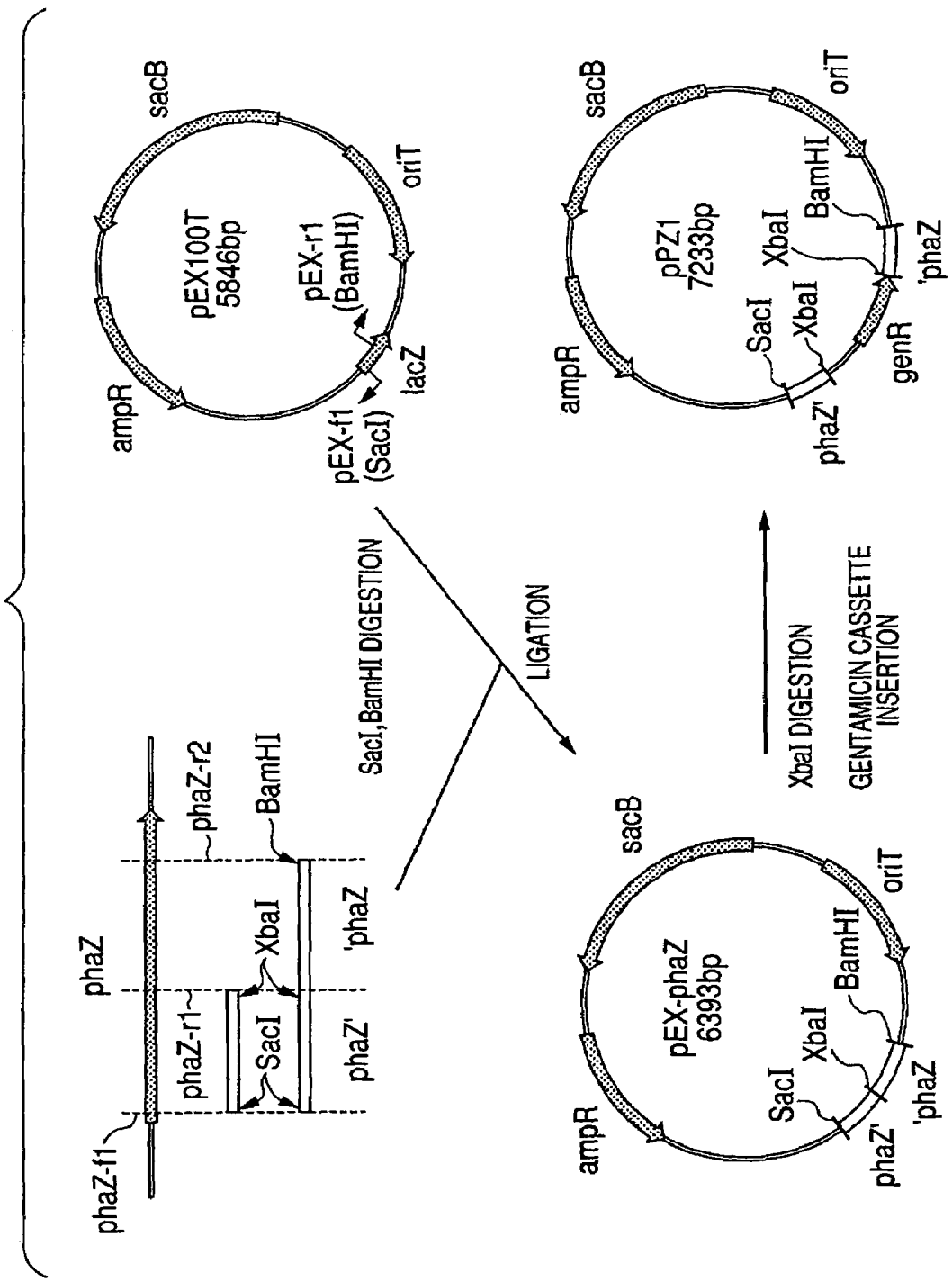
FIG. 1 illustrates the procedure for construction of the targeting vector for the polyhydroxyalkanoate depolymerase gene exemplified in Embodiment 1.

The bacterium for producing polyhydroxyalkanoate provided by the present invention is not particularly limited but can be, a bacterium for producing polyhydroxyalkanoate, among the microbes known to produce polyhydroxyalkanoate, containing the polyhydroxyalkanoate depolymerase gene on the chromosome which is homologous enough to the DNA shown in (a) or (b) below:

(a) a DNA, which contains the base sequence shown in SEQ ID NO:1, or a portion thereof;

(b) a DNA, which hybridizes under stringent conditions with the DNA having the complementary base sequence of the DNA containing the base sequence shown in SEQ ID NO:1, or a portion thereof, so that the DNA can undergo homologous recombination with the polyhydroxyalkanoate depolymerase gene under a physiological condition, that is in the microbe cells, and the polyhydroxyalkanoate depolymerase gene can be disrupted. Such microbes include *Pseudomonas oleovorans* (Makromol. Chem., 191, 1957-1965 (1990) and Macromolecules, 24, 5256-5260 (1991), *Pseudomonas putida* (Can. J. Microbiol., 41, 32-43 (1995) and Polymer International, 39, 205-213 (1996)), *Pseudomonas resinovorance* (Appl. Environ. Microbiol. 58 (2), 746 (1992)), *Pseudomonas* sp. 61-3 strain (Int. J. Biol. Macromol., 16 (3), 119 (1994)), *Pseudomonas cichorii* YN2 (FERM BP-7375), *Pseudomonas cichorii* H45 (FERM BP-7374), *Pseudomonas jessenii* P161 (FERM BP-7376) and the like, but not limited to these as long as it has the homology described above, and bacterium for producing polyhydroxyalkanoates that will be discovered in the future may also be included in the present invention.

The present inventors searched a microbe capable of producing PHA containing 3-hydroxyphaenylvalerate monomer unit using phenyl valeric acid as substrate. As a result, a microbial strain having the desired capability was successfully isolated from soil and designated as YN21 strain.

The search using the bacterial characteristics described below, based on Bergey's Manual of Systematic Bacteriology, Volume 1 (1984) and Bergey's Manual of Determinative Bacteriology, ninth edition (1994), revealed that YN21 strain belongs to the genus *Pseudomonas*. Thus, this bacterial strain was designated as *Pseudomonas* sp. YN21.

*Pseudomonas* sp. YN21, the microbe that the present inventors isolated from soil as a bacterial producer of polyhydroxyalkanoates with unusual substituents, is suitably provided especially for the present invention. The YN21 strain is deposited as the deposit No. "FERM BP-08569" in Patent Microorganism Depository Center, National Institute of Advanced Industrial Science and Technology, (Chuoh No. 6, 1-1 Higashi, 1-chome, Tsukuba-City, Ibaragi-Prefecture). The bacterial characteristics of YN21 strain are listed below.

<The Bacterial Characteristics of YN21 Strain>

1) Morphological Characteristics

Size and shape of cell: *bacillus*, 0.8 μm×1.5-2.0 μm

Polymorphism of cell: no

Motility: yes

Spore formation: no

Gram staining:−

Appearance of colony: round, smooth periphery, low convex, smooth surface, lustrous, semitransparent 2) Physiological Characteristics Catalase activity:+

Oxidase activity:+

O/F test: oxidative

Nitrate reduction test:+

Indole production:−

Arginine dihydrolase:+

Esculin hydrolysis:−

Gelatin hydrolysis:−

Fluorescent dye production in King's B agar:+

Accumulation of poly-β-hydroxybutyric acid:−

Hydrolysis of Tween 80:+

Growth at 41° C.:−

Reduction of gluconic acid:−

Levan production:−

Putrefaction of potato:−

Tobacco hypersensitivity:−

Sucrose:−

Casein:−

Tyrosinase:+

Hydrogen sulfide:−

Pectin:−

Lecithinase:−

Litmus milk: B

Starch:−

3) Substrate Utilization

Glucose:+

L-arabinose:+

D-mannose:+

D-mannitol:−

Maltose:−

Gluconic acid:+

D-xylose: (+)

Raffinose:−

Salicin:−

Glycerin:+

D-cellobiose:−

D-melezitose:−

Lactose:−

Galactose:+

D-sorbitol:−

α-methyl-D-glucoside:−

D-ribose: (+)

Sucrose:−

Inositol:−

D-fructose:+

L-rhamnose:−

D-arabinose:−

Dulcitol:−

Melibiose:−

Adonitol:−

Starch:−

Erythritol:−

Trehalose:−

Betaine:+

DL-lactic acid:+

D-tartaric acid:−

L-tartaric acid: (+)

Meso-tartaric acid:+ n-capric acid:+

L-malic acid: (+)

Citric acid:+

D-Saccharate:+

Levulinic acid:+

Mesaconic acid:−

Malonic acid:+

Succinic acid:+

Acetic acid:+

Propionic acid:+ n-butyric acid:+

Formic acid:−

Glutaric acid:+

D-quinic acid:+

Sebacic acid:+ p-hydroxybenzoic acid:+

Anthranilic acid:−

Pelargonic acid:+

Glyceric acid:+

γ-aminobutyric acid:+

L-leucine:+

L-serine:+

Histidine:+

L-isoleucine:+

L-arginine:+

β-alanine:+

L-tyrosine:+

L-valine:+

Homoserine:−

Sarcosine:+

Triacetin:+

Trigonelline:+

5-phenylvaleric acid:+

3-hydroxybutyric acid:+

L-asparagine:+

YN21 strain can be differentiated from an existing strain, *Pseudomonas cichorii* YN2 (FERM BP-7375), in physiological characteristics and substrate utilization such as nitrate reduction, indole production, glucose acidification, ariginine dihydrolase activity, D-mannose utilization and the like. Further, YN21 strain is different in characteristics from other existing strains: *Pseudomonas cichorii* H45 (FERM BP-7374) in nitrate reduction, arginine dihydrolase activity, L-arabinose utilization and D-mannitol utilization; *Pseudomonas jessenii* P161 (FERM BP-7376) in D-mannitol utilization; and *Pseudomonas putida* P91 strain (FERM BP-7373) in nitrate reduction, L-arabinose utilization, and D-mannose utilization.

The bacterium for producing polyhydroxyalkanoate of the present invention, in which the gene coding for polyhydroxyalkanoate depolymerase is disrupted, can be obtained by subjecting a bacterium for producing polyhydroxyalkanoate to: mutagenic treatment resulting in a change in the base sequence of the gene coding for polyhydroxyalkanoate depolymerase; integration of a transposon into the base sequence of the gene coding for the enzyme; and genetically engineered modifications such that the gene coding for the enzyme is not expressed, for example antisense gene inhibition and further selective gene disruption.

Chemical mutagens useful for inducing mutation include alkylating agents, for example, N-methyl-N'-nitro-N-nitrosoguanidine (NTG), ethyl methanesulfonate (EMS), diethyl sulfate (DES) and the like. Chemicals, which deaminate DNA bases, such as hydroxylamine, nitrite and the like, are also useful. Ionizing radiation (γ- and X-ray) and ultraviolet (UV) irradiation are physical mutagens useful for inducing mutations.

To obtain a strain having the polyhydroxyalkanoate depolymerase gene disrupted from a randomly mutated bacterial strain, the mutated bacterial strain may be, for example, subjected to the primary screening by culturing it on agar plates containing an alkanoic acid which may be used as a constituent unit of PHA, and identifying bacteria capable of synthesizing PHA in their cells by fluorescent staining of the intracellular PHA using Nile red and the like. Then bacteria incapable of degrading/reusing intracellular PHA in nutrient poor condition are identified by fluorescent remnant of intracellular PHA using Nile red staining in the secondary screening.

To obtain a bacterium for producing polyhydroxyalkanoate, in which the gene coding for polyhydroxyalkanoate depolymerase is disrupted by a selective gene disruption method, the homologous recombination using linear DNA may be used. However, the bacterium for producing polyhydroxyalkanoate, in which the gene is disrupted, can be obtained with less damage to the bacteria and with better efficiency by using in particular the vector targeting the polyhydroxyalkanoate depolymerase gene, which is disclosed as one of the invention related to the present application.

Figure 4A:
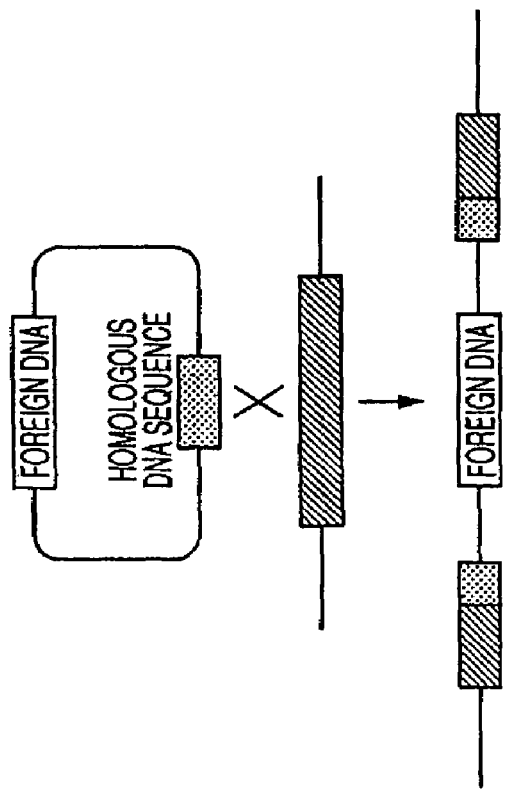
FIGS. 4A and 4B illustrate the methods of selective gene disruption by the gene disruption by insertion and gene replacement method.
Figure 4B:
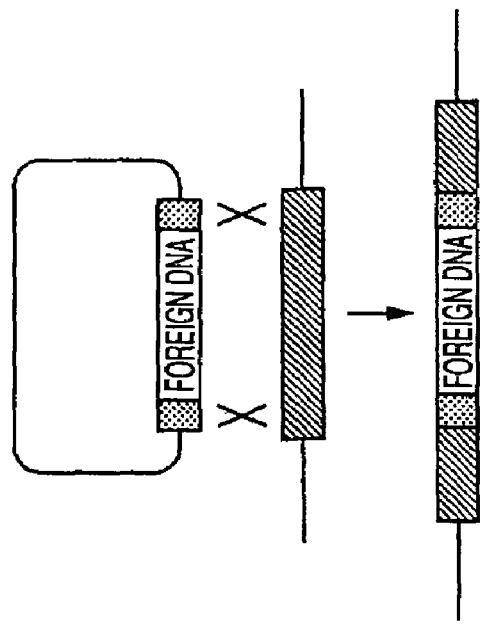

In general, the selective gene disruption method to the target site on the chromosome by homologous recombination is used for studying the function of the gene and for selective disruption of the gene which is involved in undesired characteristics for growing microbes for practical use. The two disruption method, the gene disruption by insertion and the gene replacement method, have been used (FIGS. 4A and 4B). These methods are based on a basic principle that a foreign desired gene included in the DNA of the foreign target gene is integrated into the target DNA sequence of the endogenous genomic DNA by inducing artificially a genetic homologous recombination, which could occur naturally in the living body of organisms, between the endogenous genomic DNA on the chromosome of the organism and foreign targeting DNA (targeting vector). Either of the aforementioned gene disruption by insertion or gene disruption by replacement may be used for producing the bacterium for producing polyhydroxyalkanoate of the present invention, in which the gene coding for polyhydroxyalkanoate depolymerase is disrupted.

The gene targeting vector in the present invention means a DNA construct used for disrupting the target DNA by homologous recombination, which forms the gene coding for polyhydroxyalkanoate depolymerase in the endogenous genomic DNA of the bacterium for producing polyhydroxyalkanoate. Here, "disrupting gene" means the change in DNA sequence described below introduced into a portion of the endogenous genome by homologous recombination between the targeting DNA and the endogenous genomic DNA.

(1) A deletion of a portion of the DNA sequence of the target DNA (2) A replacement of a portion of the DNA sequence of the target DNA with a foreign DNA (3) An insertion of a foreign DNA into the DNA sequence of the target DNA The change in the DNA sequence achieved by the gene disruption by insertion is the change by the (3). The change in the DNA sequence achieved by the gene disruption by replacement is the change by the (1), (2) or (3). By these changes, the gene coding for polyhydroxyalkanoate depolymerase in the endogenous genomic DNA of the bacterium for producing polyhydroxyalkanoate loses the function practically, and transcription/translation of the polyhydroxyalkanoate depolymerase gene or biosynthesis of polyhydroxyalknoate depolymerase protein with activity can be prevented.

The basic structure of the targeting vector for the polyhydroxyalkanoate depolymerase gene, related to the present invention, may be varied depending on the procedures for the gene disruption and can assume the following 3 basic structures.

(I) The structure is basically composed of the DNA for homologous recombination, shown in following (a) or (b), and the region for disrupting the desired gene linked to the vector.

(a) DNA containing the base sequence shown in SEQ ID NO:1 or a portion thereof.

(b) DNA hybridizing under stringent conditions with a DNA which is complementary to the DNA containing the base sequence shown in SEQ ID NO:1, or a portion thereof.

(II) In the case where the target gene is disrupted by the gene insertion disruption method, the gene targeting vector of the present invention is composed of the basic structure containing a DNA shown in following (a) or (b) as the homologous DNA sequence (homologous region) to the target DNA sequence, and also containing a desired foreign DNA which is foreign to the endogenous genomic DNA;

(a) DNA containing the base sequence shown in SEQ ID NO:1 or a portion thereof.

(b) DNA hybridizing under stringent conditions with a DNA which is complementary to the DNA containing the base sequence shown in SEQ ID NO:1, or a portion thereof.

(III) In the case where the target gene is disrupted by the gene replacement disruption method, the gene targeting vector of the present invention is composed of the basic structure containing a DNA shown in following (a) or (b) as the homologous DNA sequence (homologous region) to the target DNA sequence, and in which a desired foreign DNA which is foreign to the endogenous genomic DNA is inserted into the DNA sequence (homologous region) homologous to the target DNA sequence;

(a) DNA containing the base sequence shown in SEQ ID NO:1 or a portion thereof.

(b) DNA hybridizing under stringent conditions with a DNA which is complementary to the DNA containing the base sequence shown in SEQ ID NO:1, or a portion thereof.

Here, in the basic structure (I), (II) and (III), the DNA that "hybridizes under the stringent condition" is the DNA described below. That is, it is the DNA which (1) forms a DNA-DNA hybrid with the DNA containing the base sequence shown in SEQ ID NO:1 under a high ionic concentration [including, for example, 6×SSC (900 mM of sodium chloride, 90 mM sodium citrate) and the like] and at the temperature of 65° C. and in which (2) the hybrid is maintained after washing under a low ionic concentration [including, for example, 0.1×SSC (15 mM of sodium chloride, 1.5 mM of sodium citrate) and at the temperature of 65° C. for 30 min. In particular, for example, DNAs having the base sequence shown in SEQ ID NO:1, in which a portion is deleted, replaced or added to the extent that the disruption function to the desired gene is not impaired, are included. Such DNA may be natural cloned DNA, natural cloned DNA with artificially introduced base deletion, replacement or addition, or artificially synthesized DNA. Further, in the basic structure (I), (II), (III), "DNA shown as (a) or (b), or a portion thereof" is not necessary for coding for a protein having polyhydroxyalkanoate depolymerase activity but may have such a homology that it can cause homologous recombination with the polyhydroxyalkanoate depolymerase gene on the chromosome under the physiological condition, e.g., in the microbial cells, to disrupt the polyhydroxyalkanoate depolymerase gene. Such homology may be preferably 90% or above, and more preferably 95% or above. Still further, if the DNA, which is used for producing a strain of the microbe in which polyhydroxyalkanoate depolymerase gene is disrupted, is large enough so that the DNA can undergo homologous recombination with the polyhydroxyalkanoate depolymerase gene on the chromosome and disrupt the same by doing so, the DNA may be a portion of the DNA shown in aforementioned (a) or (b). Here, a portion means that the length is preferably 50 bases or longer, or more preferably 100 base or longer while keeping the capability of disrupting the desired gene.

Particular examples of "a portion" of DNA shown in (a) or (b) that is placed in the gene targeting vector include SEQ ID NO:11, SEQ ID NO:12, SEQ ID NO:13, SEQ ID NO:14 and SEQ ID NO:15.

The vector in the basic structure (I) is not particularly limited, and general vectors with wide host range may be used and include, for example, pJRD215 (Davidson et al., Gene, 51, 275-280 (1987)) and pBBR1MCS series (Kovach et al., Gene, 166, 175-176 (1995)) and the like.

The "foreign DNA" in the basic structure (II), (III) includes, for example, the marker gene, the reporter gene, the gene amplifying gene, the gene expression control DNA sequence, which can be provided with characteristics that lead to a substantial functional disruption of the polyhydroxyalkanoate depolymerase gene by introducing deletion, replacement or insertion into the target DNA sequence in the endogenous genomic DNA, or DNA sequence containing one or more of these. Here, the "marker gene" includes any of the marker genes which are used normally in the art of the genetic engineering field. Examples include the resistant genes to antibiotics such as tetracycline, ampicillin, gentamicin or kanamycin. Further, examples of the "reporter gene" include the genes of luciferase, green fluorescent protein (GFP), β-lactamase and the like. Still further, examples of the "gene amplifying gene" include a DNA sequence containing desired primer binding sequences by which a specific gene amplification product of the disrupted strain can be obtained by the PCR method using the chromosomal DNA as a template.

When the Mob site containing the conjugative transfer origin gene (OriT) is introduced to the gene targeting vector of the basic structure (II) and (III), and *Escherichia coli* mobilizer strain, for example, S17-1 strain (ATCC 47055) is transformed by the vector and used as a plasmid supplying bacteria, the vector can be introduced into the bacterium for producing polyhydroxyalkanoate more efficiently with less damage thereto and thus it is possible to obtain more easily and more efficiently the bacterial strains, in which the polyhydroxyalkanoate depolymerase gene is disrupted, and thus this method is more favorable. This is because, since *E. coli* mobilizer strain contains the tra gene, the mob$^+$, tra$^-$ gene targeting vector can be conjugatively transferred without the help of the helper plasmid (R. Simon et al. (1983) Bio-Technology 1: 784).

It is preferable for the gene targeting vector of the basic structure (III) to contain a gene which leads plasmid recipient bacteria to death (susceptibility gene) under a certain condition.

As a susceptibility gene, for example, the Levansucrase (sacB) gene derived from *Baccilus subtilis* can be suitably used in the present invention, because it has been found that many gram-negative bacteria therewith are killed in the medium containing sucrose at 5 wt. % or more (Gay et al. J. Bacteriol. 164, 918), and also confirmed by the present inventors that the gene functions in *Pseudomonas* sp. YN21 strain.

In the gene targeting vector of the basic structure (III), the site of insertion of the selection marker to the aforementioned DNA shown in (a) or (b) or a portion thereof is at between 1-9, preferably 2-8 and more preferably 4-6, when the length of the DNA shown in (a) or (b) or a portion thereof, in which the selection marker is inserted, is assumed to be 10. When the site of insertion of the selection marker is biased to one end of the DNA shown in (a) or (b) or a portion thereof, the yield of double homologous recombinants, using the activity of the susceptibility gene, is lowered, and thus this is not preferable.

To construct the gene targeting vector of the basic structure (I), (II) or (III), each DNA that is a composing element of the aforementioned basic structure may be integrated into the vector using normal technique of molecular biology, but the utilization of a mobile vector, which contains a replication gene that is incompatible with the replication gene of the bacterium for producing polyhydroxyalkanoate, the origin of conjugative gene and susceptibility gene, would be useful because the targeting vector for the polyhydroxyalkanoate depolymerase gene of the present invention can be produced with fewer steps. Such mobile vectors include, for example, pEX100T (ATCC 87436), pJQ200 (ATCC 77482), pDMS197 (ATCC 87694), pRE107 (ATCC 87691) and the like and can be used suitably for construction of the targeting vector for the polyhydroxyalkanoate depolymerase gene of the present invention.

For example, to construct the gene targeting vector of the basic structure (III), the DNA shown in aforementioned (a) or (b) or a portion thereof and the selection marker may be integrated to the aforementioned mobile vector. There is no restriction in the order of integration for these. For example, the aforementioned mobile vector is treated with an appropriate restriction enzyme, and a DNA fragment thus obtained is mixed with the DNA shown in aforementioned (a) or (b) or a portion thereof and the mixture is treated with DNA ligase. Next, a portion of the vector or the DNA shown in aforementioned (a) or (b) or a portion thereof integrated into the vector are cleaved by the treatment of a restriction enzyme that recognize the different site from the aforementioned restriction enzyme. The fragment thus obtained is mixed with a DNA fragment that contains the aforementioned selection marker and treated with DNA ligase to insert the selection marker to the vector. Further, in the steps of the construction, treatments known in the arts may be performed such as addition of linkers, formation of blunt ends and the like.

To disrupt the polyhydroxyalkanoate depolymerase gene of the bacterium for producing polyhydroxyalkanoate using the gene targeting vector of the basic structure (I), this gene targeting vector is introduced into the bacterium for producing polyhydroxyalkanoate. The method for introducing the gene targeting vector can be appropriately selected from the well known methods to a person skilled in the arts such as contacting to competent cells, electroporation and the like. Next, the primary screening is carried out by growing the microbial producer on an agar plate containing alkanoic acid which may be used as a constituent unit of PHA, and by identifying the bacteria capable of synthesizing PHA in the cells by fluorescent staining of the intracellular PHA using Nile red and the like. Then bacteria incapable of degrading/reusing intracellular PHA in nutrient poor condition are identified by fluorescent remnant of intracellular PHA using Nile red staining in the secondary screening.

Disruption of the polyhydroxyalkanoate depolymerase gene of the bacterium for producing polyhydroxyalkanoate using the gene targeting vector of the basic structure (II) or (III) may be carried out in the same manner as the case of the gene targeting vector of the basic structure (I). First the aforementioned mobilizer strain of *E. coli* is transformed by this gene targeting vector. Next, the gene targeting vector is transferred into the bacterium for producing polyhydroxyalkanoate by using conjugative transfer between the transformed mobilizer strain of *E. coli* and the bacterium for producing polyhydroxyalkanoate. By selecting with the aforementioned selection marker, the strain may be obtained in which the polyhydroxyalkanoate depolymerase gene is disrupted as a result of homologous recombination between the gene targeting vector and the chromosome DNA. Further, since in the chromosome of the host, the bacterium for producing polyhydroxyalkanoate, and the gene targeting vector contain 2 homologous region at the front and the end of the aforementioned selection marker, most of the homologous recombinants obtained at this stage are two kinds with structures having the sequence derived from the gene targeting vector inserted at the different site, and it is believed to be that the ratio of the homologous recombinants having the crossing at the both of two homologous regions at the front and the end of the selection marker at the same time is very low. However, the polyhydroxyalkanoate depolymerase gene is disrupted by inserting the sequence derived from the gene targeting vector.

Next, in the case where the gene targeting vector of the basic structure (III) is used, the selection based on the function of the susceptibility gene is carried out. By this selection, a variant strain may be obtained from the plasmid recipient bacteria in which strain, among the sequences derived from the gene targeting vector inserted into the chromosome of the recombinants selected by the aforementioned selection marker, the mobile vector portion is deleted. This is achieved by the homologous recombination at the other homologous region which was not used at the homologous recombination of the previous step. Thus, the two kinds of recombinants having different chromosomal structures at the previous step becomes the recombinant having the same chromosomal structure (the polyhydroxyalkanoate depolymerase gene is splitted by the selection marker).

Disruption of the polyhydroxyalkanoate depolymerase gene in the recombinants obtained using the targeting vector of the present invention which is directed to the polyhydroxyalkanoate depolymerase gene may be confirmed by any one of the following methods: by determining the loss of the polyhydroxyalkanoate depolymerase activity in the recombinant by the method described above; by Southern hybridization after digesting the chromosomal DNA of the recombinant; or by the PCR method using the chromosomal DNA template and appropriate primers.

Since the targeting vector for polyhydroxyalkanoate depolymerase gene of the present invention replicates and amplifies autonomously in an appropriate host cells, copies of this vector can be produced by culturing the transformant which is obtained by introducing this vector to host cells. Such host cells that may be used without distinction include gram positive or gram negative bacteria, higher or lower cells, animal or plant cells, as long as the cell can be transformed by the targeting vector for polyhydroxyalkanoate depolymerase gene, and the vector can be stably maintained and replicated in the cell. To introduce the targeting vector for the polyhydroxyalkanoate depolymerase gene to the host cells, the method can be selected appropriately from those well known to a person skilled in the arts, such as contacting the targeting vector for the polyhydroxyalkanoate depolymerase gene to competent cells, electroporation and the like.

For normal culturing of the polyhydroxyalkanoate depolymerase gene disrupted strain used for the PHA production method of the present invention, for example, preparing storage bacteria, growing to obtain the number of bacteria and to maintain the active condition needed for PHA production and the like, a medium containing needed components for growth of the disrupted strain to be used is selected appropriately. For example, any kind of media may be used, such as general natural media (meat broth media, yeast extract and the like) and synthetic media supplemented with nutrient source, as long as they do not have bad effects on the growth and survival of the disrupted strain.

Any culture method, such as liquid culture, solid culture and the like may be used as long as the disrupted strain grows and PHA is produced. Further, batch culture, fed batch culture, semi-continuous culture, continuous culture and the like may be used without distinction. In liquid batch culture style, oxygen is supplied by shaking flask method and by mixed aeration method by a jar fermentor. Also, a multiple steps procedure may be adopted by connecting a multiplicity of these steps.

The composition and structure of PHA, in particular, variety of unusual PHA having substituents in the side chain, produced by the strain, in which the polyhydroxyalkanoate depolymerase gene is disrupted, is determined by the nature of the isogenic strain, in which the polyhydroxyalkanoate depolymerase gene is not disrupted. When *Pseudomonas* sp. PZ1 strain is used, which is isogenic strain to *Pseudomonas* sp. YN21 strain and in which the polyhydroxyalkanoate depolymerase gene is disrupted, polyhydroxyalkanoate can be produced, in which polymer molecules contain at least one kind of polymer unit which is selected from the group consisting of polymer units with chemical formula from [1] to [16] shown below.

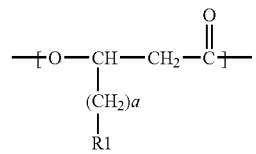

wherein the combination of R1 and a is at least one selected from the group consisting of polymer units described below:

(1) a polymer unit in which R1 is a hydrogen atom (H) and a is any one of integers from 1 to 10; (2) a polymer unit in which R1 is a halogen atom and a is any one of integers from 1 to 10; (3) a polymer unit in which R1 is Formula 2

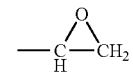

and a is any one of integers from 1 to 8.

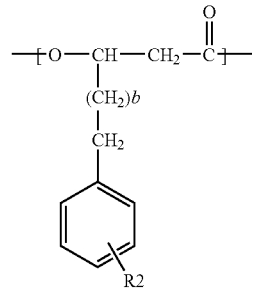

wherein R2 is a substitution group to the aromatic ring, and represents any one selected from the group consisting of hydrogen atom (H), halogen atom, CN group, $NO_2$ group, COOR' (R': any one of H, Na, and K) group, $CH_3$ group, $C_2H_5$ group, $C_3H_7$ group, $CH=CH_2$ group, $CF_3$ group, $C_2F_5$ group and $C_3F_7$ group, and b represents any one of integers from 0 to 7.

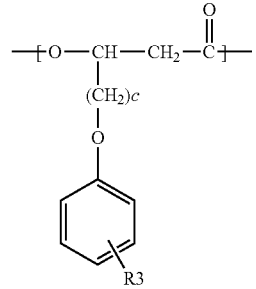

wherein R3 is a substitution group to the aromatic ring, and represents any one selected from the group consisting of hydrogen atom (H), halogen atom, CN group, $NO_2$ group, $CH_3$ group, $C_2H_5$ group, $C_3H_7$ group, $SCH_3$ group, $CF_3$ group, $C_2F_5$ group and $C_3F_7$ group, and c represents any one of integers from 0 to 7.

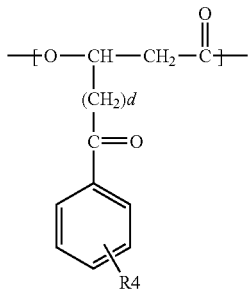

[4]

wherein R4 is a substitution group to the aromatic ring, and represents any one selected from the group consisting of hydrogen atom (H), halogen atom, CN group, $NO_2$ group, $CH_3$ group, $C_2H_5$ group, $C_3H_7$ group, $CF_3$ group, $C_2F_5$ group and $C_3F_7$ group, and d represents any one of integers from 0 to 7.

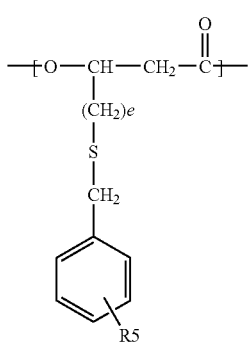

[5]

wherein R5 is a substitution group to the aromatic ring, and represents any one selected from the group consisting of hydrogen atom (H), halogen atom, CN group, $NO_2$ group, COOR' (R': any one of H, Na, K, $CH_3$ and $C_2H_5$) group, $SO_2R''$ (R'': any one of OH, ONa, OK, halogen atom, $OCH_3$ and $OC_2H_5$) group, $CH_3$ group, $C_2H_5$ group, $C_3H_7$ group, $CH(CH_3)_2$ group and $C(CH_3)_3$ group, and e represents any one of integers from 1 to 8.

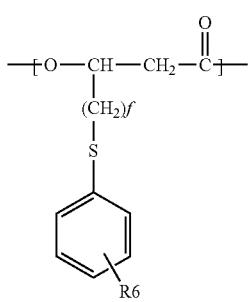

[6]

wherein R6 is a substitution group to the aromatic ring, and represents any one selected from the group consisting of hydrogen atom (H), halogen atom, CN group, $NO_2$ group, COOR' (R': any one of H, Na, K, $CH_3$ and $C_2H_5$) group, $SO_2R''$ (R'': any one of OH, ONa, OK, halogen atom, $OCH_3$ and $OC_2H_5$) group, $CH_3$ group, $C_2H_5$ group, $C_3H_7$ group, $CH(CH_3)_2$ group and $C(CH_3)_3$ group, and f represents any one of integers from 1 to 8.

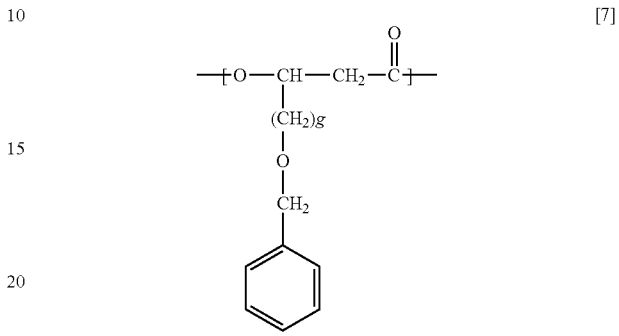

[7]

wherein g represents any one of integers from 1 to 8.

[Formula 9]

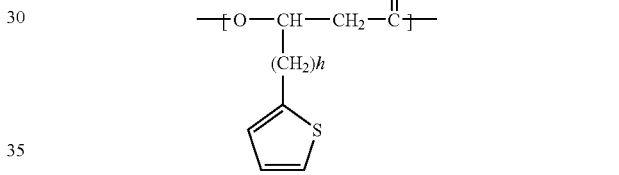

[8]

wherein h represents any one of integers from 1 to 8.

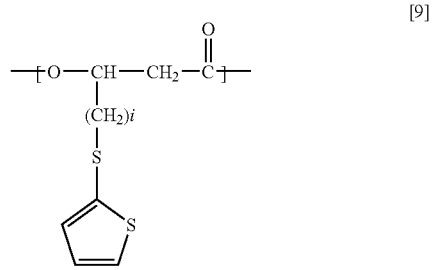

[9]

wherein i represents any one of integers from 1 to 8.

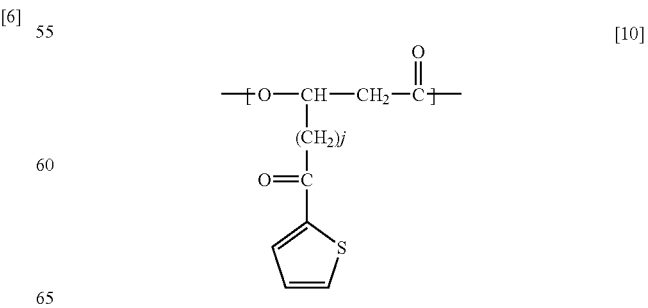

[10]

wherein j represents any one of integers from 1 to 8.

[Formula 12]

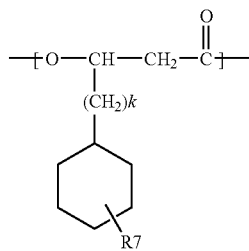
[11]

wherein R7 is a substitution group to cyclohexyl group, and represents any one selected from the group consisting of hydrogen atom (H), halogen atom, CN group, $NO_2$ group, $CH_3$ group, $C_2H_5$ group, $C_3H_7$ group, $CF_3$ group, $C_2F_5$ group and $C_3F_7$ group, and k represents any one of integers from 0 to 8.

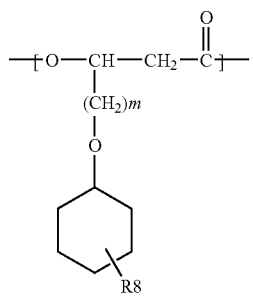
[12]

wherein R8 is a substitution group to cyclohexyloxy group, and represents any one selected from the group consisting of hydrogen atom (H), halogen atom, CN group, $NO_2$ group, $CH_3$ group, $C_2H_5$ group, $C_3H_7$ group, $CF_3$ group, $C_2F_5$ group and $C_3F_7$ group, and m represents any one of integers from 1 to 8.

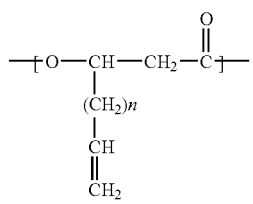
[13]

wherein n represents any one of integers from 1 to 8.

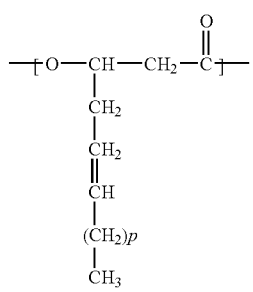
[14]

wherein p represents any one of integer 3 or 5.

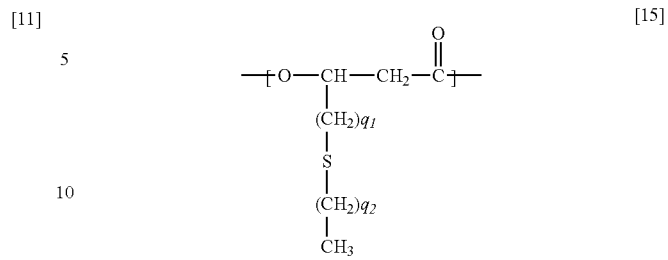
[15]

wherein $q_1$ represents any one of integers from 1 to 8 and $q_2$ represents any one of integers from 0 to 8.

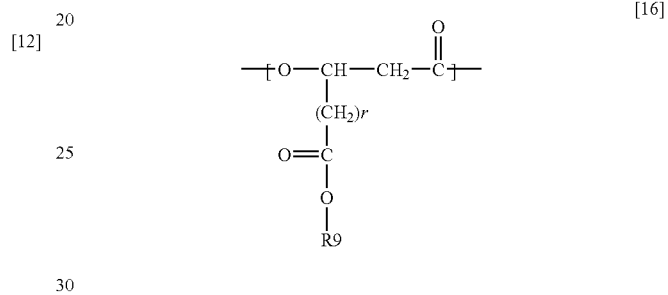
[16]

wherein R9 represents hydrogen atom (H), Na atom or K atom, and r represents any one of integers from 1 to 8.

In the case where PHA containing 3-hydroxyalkanoate as monomer units is produced, using the polyhydroxyalkanoate depolymerase gene disrupted strain, an inorganic medium and the like may be used which at least contains corresponding alkanoic acid or alkane as materials for PHA production, and a carbon source for the growth of the disrupted strain.

Medium components derived from natural sources, such as yeast extract, polypeptone, meat extract, casamino acid and the like, may be used as a carbon source for growth. Further, any compound may be used, such as sugars, organic acids which are involved in the TCA cycle (organic acids generated as intermediates in the TCA cycle, or generated after one or two steps of biochemical reactions from the TCA cycle intermediates) or salts thereof and the like as long as it can produce acetyl CoA without going through the β-oxidation cycle, and may be chosen depending on the utility as substrate for the bacterial strain to be used.

Among these compounds, examples of sugars include: aldoses such as glyceroaldehyde, erythrol, arabinose, xylose, glucose, galactose, mannose and fructose; alditols such as glycerol, erythritol and xylitol; aldonic acids such as gluconic acid; uronic acids such as glucuronic acid, and galacturonic acid; disaccharides such as maltose, sucrose and lactose, and one or more of the compounds selected from the examples can be used favorably.

Further, examples of organic acid or a salt thereof include pyruvic acid, oxaloacetic acid, citric acid, isocitric acid, keto-glutaric acid, succinic acid, fumaric acid, malic acid, lactic acid, and one or more of the compounds selected from the examples can be used favorably.

Among these compounds, it is preferable to use sugars in particular, and among others it is more preferable that at least one is selected from the group consisting of glucose, fructose and mannose.

As a method to make the polyhydroxyalkanoate depolymerase gene disrupted strain produce and accumulate PHA, it has been observed that sometimes the productivity is improved by transferring the bacteria, after sufficiently grown, to a medium with limited nitrogen source such as ammonium chloride, and by culturing after adding a compound which becomes the substrate for the target unit. In particular, the multi-step method, in which a multiplicity of the aforementioned processes are linked, may be adopted. For example, in this method, the bacteria may be grown in an inorganic medium containing from about 0.05 wt. % to 5.0 wt. % of glucose, and from about 0.01 wt. % to 1.0 wt. % of alkanoic acid or alkane from the late log phase to the steady state phase, and after recovering the bacteria by centrifugation or the like, further cultured in an inorganic medium containing from about 0.01 wt. % to 1.0 wt. % of alkanoic acid or alkane with limited or practically no nitrogen source.

Any inorganic medium may be used in the aforementioned culture method as long as it contains components on which bacteria can grow, such as phosphate source (for example, phosphate salts and the like) and nitrogen source (for example, ammonium salts, nitrate salts and the like), and for example, the inorganic medium may include MSB medium, E medium (J. Biol. Chem., 218, 97-106 (1956)), M9 medium and the like.

The composition of M9 medium used in the embodiments of the present invention is as follows:

$Na_2HPO_4$: 6.2 g $KH_2PO_4$: 3.0 g

NaCl: 0.5 g $NH_4Cl$: 1.0 g (for 1l of medium, pH 7.0)

Further, for better growth and PHA production, it is preferable to add about 0.3% (v/v) of the following solution of trace components to the inorganic medium described above.

Trace components solution

Nitrilotriacetic acid: 1.5 g $MgSO_4$: 3.0 g $MnSO_4$: 0.5 g

NaCl: 1.0 g $FeSO_4$: 0.1 g $CaCl_2$: 0.1 g $CoCl_2$: 0.1 g $ZnSO_4$: 0.1 g $CuSO_4$: 0.1 g $AlK(SO_4)_2$: 0.1 g $H_3BO_3$: 0.1 g $Na_2MoO_4$: 0.1 g $NiCl_2$: 0.1 g (in 1 l)

The culture temperature may be at any temperature as long as the polyhydroxyalkanoate depolymerase gene disrupted strain can grow well and for example, 15-40° C., preferably 20-35° C., more preferably from about 20° C. to 30° C. is suitable.

As a particular example, desired PHA, which contains very little or no contaminating monomer units that are not the target product, can be extracted by culturing the host cells in an inorganic medium and the like containing from 0.05 wt. % to about 5.0 wt. % of D-glucose and from 0.01 wt. % to about 1.0 wt. % of alkanoic acid or alkane and by recovering the host cells at the time from late log phase to steady state phase. Such PHA is in general composed of only R form units and thus an isotactic polymer. In place of D-glucose, the same amount of organic acids involved in the TCA cycle, east extract, and polypeptone may be given. Also, a combination of these may be used.

To obtain PHA from the culture medium in the present invention, a usual method may be applied. If PHA is excreted into the culture medium, extraction/purification from culture medium is the carried out, and if PHA is accumulated in the cells, extraction/purification from the cells is conducted. For example, to recover PHA from cell body of cultured microbes, extraction with organic solvent such as chloroform and the like is in common and simplest, but in some cases, apart from chloroform, dioxane, tetrahydrofuran, acetonitrile and acetone may be used. Further, in the environment where organic solvents are difficult to use, the method for recovering PHA may be to remove cell body components other than PHA by treatment with: a surface active agent such as SDS and the like; enzyme such as lysozyme; and drug such as EDTA.

Further, the culturing of the microbes of the present invention, production and accumulation in cell body of PHA by the microbes of the present invention, as well as the recovery of PHA from cell body in the present invention are not limited to the methods described above.

Embodiment 1

Since the result of pre-investigation of the drug resistance of the bacterium for producing polyhydroxyalkanoate, *Pseudomonas* sp. YN21 strain (FERM BP-08569) revealed that it is resistant to ampicillin and chloramphenicol and sensitive to gentamicin, the targeting vector for the polyhydroxyalkanoate depolymerase gene was constructed using the gentamicin resistant gene as a marker. The gene disruption vector constructed is a circular plasmid DNA (pPZ1 (SEQ ID NO:10)) containing the partial base sequence from the base number 36 to 708 of the base sequence shown in SEQ ID NO:1 (the base sequence is replaced at the base 345 of the SEQ ID NO:1 so that it can be cut by XbaI). Following is the description of the procedure. FIG. 1 illustrates the summary of the procedure.

1) Preparation of Genomic DNA

*Pseudomonas* sp. YN21 strain was cultured in M9 medium containing 0.5% (w/v) of polypeptone at 30° C. for 24 hr. After harvesting the cells from the culture medium, the genomic DNA of YN21 strain was prepared using Wizard Genomic DNA Purification System (Promega Inc.)

2) Preparation of DNA Fragment for Insertion

PCR (polymerase chain reaction) was carried out using the genomic DNA of Y21 strain as a template and DNAs with the base sequences shown in phaZ-f1 (SEQ ID NO:2) and phaZ-r1 (SEQ ID NO:3) as primers. The following reaction mixture was prepared.

TABLE 1

| | |
|---|---|
| Template (genomic DNA derived from YN21) | 250 ng |
| Primer phaZ-f1 (SEQ ID NO: 2) | 250 pmol |
| Primer phaZ-r1 (SEQ ID NO: 3) | 250 pmol |
| 10 × buffer for amplification | 5 µl |
| dNTP | 400 µM |
| Taq polymerase (LA-Taq, Takara Bio Inc.) | 2.5 U |
| Sterilized distilled water | Appropriate amount |
| Total | 50 µl |

The PCR was carried out 30 cycles of a series of treatments of: denaturation [98° C. for 20 sec]; annealing [65° C. for 20 sec]; elongation [72° C. for 1 min]. PCR products were confirmed by agarose gel electrophoresis (gel concentration: 1 wt. %). As a result, a fragment of about 330 base pairs was amplified. The about 330 base pair PCR amplification product was excised out from agarose gel and the DNA fragment was recovered using MinElute Gel Extraction Kit (Qiagen Inc.). PCR was carried out using the recovered DNA fragment of about 330 base pair and a DNA with a sequence shown in phaZ-r2 (SEQ ID NO:4) as primers and the genomic DNA of YN21 strain as a template. The following reaction mixture was prepared.

TABLE 2

| | |
|---|---|
| Template (genomic DNA derived from YN21) | 250 ng |
| PCR product with about 330 base pairs | 250 pmol |
| Primer phaZ-r2 (SEQ ID NO: 4) | 250 pmol |
| 10 × buffer for amplification | 5 µl |
| dNTP | 400 µM |
| Taq polymerase (LA-Taq, Takara Bio Inc.) | 2.5 U |
| Sterilized distilled water | Appropriate amount |
| Total | 50 µl |

The PCR was carried out 30 cycles of a series of treatments of: denaturation [98° C. for 20 sec]; annealing [68° C. for 20 sec]; elongation [72° C. for 1 min]. PCR products were confirmed by agarose gel electrophoresis (gel concentration: 1 wt. %). As a result, a fragment of about 690 base pairs was amplified. The about 690 base pair PCR amplification product was excised out from agarose gel and the DNA fragment was recovered using MinElute Gel Extraction Kit (Qiagen Inc.). The base sequence of the about 690 base pair PCR product was analyzed using DNAs with the base sequences shown in phaZ-f1 (SEQ ID NO:2), phaZ-r1 (SEQ ID NO:3), a DNA with a complementary sequence to the base sequence shown in SEQ ID NO:3 and a DNA with the base sequence shown in phaZ-r2 (SEQ ID NO:4) as primers and with a Genetic Analyzer CEQ8000 (Beckman Coulter Inc.). The amplified product was confirmed to be corresponding to the partial base sequence comprising 673 bases from the base number 36 to 708 of the DNA shown in SEQ ID NO:1 (the base sequence is replaced at the base 345 of the SEQ ID NO:1 so that it can be cut by XbaI). The primers used in the PCR reactions described above, phaZ-f1 (SEQ ID NO:2), phaZ-r1 (SEQ ID NO:3) and phaZ-r2 (SEQ ID NO:4) already contained a SacI recognition site, a XbaI recognition site and a BamHI recognition site, respectively. The about 690 base pair PCR amplification product was digested with restriction enzymes BamHI and SacI.

Further, the about 690 base pair fragment (1) formed a DNA-DNA hybrid with the DNA containing the base sequence shown in (SEQ ID NO:1) by hybridizing under a high ionic concentration [6×SSC (900 mM of sodium chloride, 90 mM of sodium citrate)] at the temperature of 65° C., and (2) even after washing the hybrid under a low ionic concentration [0.1×SSC (15 mM of sodium chloride, 1.5 mM sodium citrate)] at the temperature of 65° C., it was maintained, which demonstrates that this fragment was hybridized under stringent conditions. Detection of a DNA-DNA hybrid was carried out using AlkPhos Direct Labelling and Detection System (Amersham Bioscience Inc.).

3) Preparation of Vector-DNA Fragment

PCR was carried out using pEX100T (ATCC No. 87436) as a template and DNAs with base sequences shown in pEX-f1 (SEQ ID NO:5) and pEX-r1 (SEQ ID NO:6) as primers. The following reaction mixture was prepared.

TABLE 3

| | |
|---|---|
| Template (pEX100T) | 250 ng |
| Primer pEX-f1 (SEQ ID NO: 5) | 250 pmol |
| Primer pEX-r1 (SEQ ID NO: 6) | 250 pmol |
| 10 × buffer for amplification | 5 µl |
| dNTP | 400 µM |
| Taq polymerase (LA-Taq, Takara Bio Inc.) | 2.5 U |
| Sterilized distilled water | Appropriate amount |
| Total | 50 µl |

The PCR was carried out 30 cycles of a series of treatments of: denaturation [98° C. for 20 sec]; annealing [65° C. for 20 sec]; elongation [72° C. for 6 min]. PCR products were confirmed by agarose gel electrophoresis (gel concentration: 1 wt. %). As a result, a fragment of about 5.6 kb was amplified. The primers used pEX-f1 (SEQ ID NO:5), and pEX-r1 (SEQ ID NO:6) already contained a BamHI recognition site and a SacI recognition site, respectively. After digesting the about 5.6 kb PCR product with BamHI and SacI, the 5' termini of the fragments were dephosphorylated using Intestine Alkaline Phosphatase (Takara Bio Inc.).

4) Ligation

The BamHI and SacI digestion products of the about 690 base pair DNA prepared in 2) described above (insert) and the BamHI and SacI digestion products of about 5.6 kb DNA prepared in 3) described above (vector) were ligated using DNA Ligation Kit Ver. 2 (Takara Bio Inc.). The composition of the ligation reaction mixture is shown below.

TABLE 4

| | |
|---|---|
| Insert DNA (0.3 pmol/µl) | 1 µl |
| Vector DNA (0.03 pmol/µl) | 4 µl |
| Enzyme Solution I (Included in the Kit) | 5 µl |
| Total | 10 µl |

Figure 2:
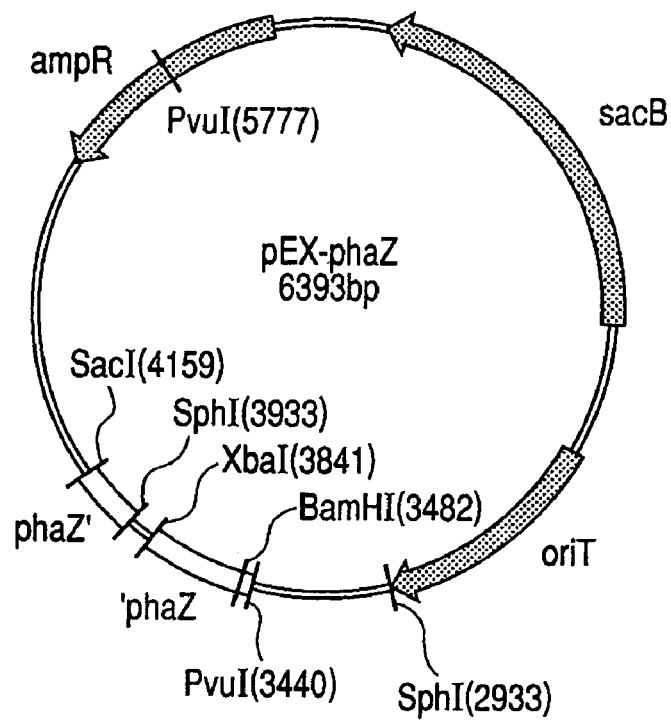
FIG. 2 is the restriction map of plasmid pEX-phaZ constructed in Embodiment 1.

After keeping the ligation mixture in a 16° C. incubator for 1 hour, the competent transformant cells of *Eschrichia coli* JM109 were produced. The colonies capable of growing on a LB agar plate containing 100 µg/ml of ampicillin were selected. As a result plasmid pEX-phaZ (SEQ ID NO:7) was obtained. The restriction map of plasmid pEX-phaZ is shown in FIG. 2.

5) Insertion of Gentamicin Cassette

After digesting plasmid pEX-phaZ prepared in 4) described above with XbaI, 5'-termini of the fragments was dephosphorylated using Intestine Alkaline Phophatase (Takara Bio Inc.). PCR was carried out using pDONR207 (Invitrogen Inc.) as a template and DNAs with base sequences shown in gen-f1 (SEQ ID NO:8) and gen-r1 (SEQ ID NO:9) as primers. The following reaction mixture was prepared.

TABLE 5

| Template (pDONR207) | 250 ng |
| Primer gen-f1 (SEQ ID NO: 8) | 250 pmol |
| Primer gen-r1 (SEQ ID NO: 9) | 250 pmol |
| 10 × buffer for amplification | 5 µl |
| dNTP | 400 µM |
| Taq polymerase (LA-Taq, Takara Bio Inc.) | 2.5 U |
| Sterilized distilled water | Appropriate amount |
| Total | 50 µl |

The PCR was carried out 30 cycles of a series of treatments of: denaturation [98° C. for 20 sec]; annealing [65° C. for 20 sec]; elongation [72° C. for 1 min]. PCR products were confirmed by agarose gel electrophoresis (gel concentration: 1 wt. %). As a result, a fragment of about 850 base pair was amplified. The each primer used, gen-f1 (SEQ ID NO:8) and gen-r1 (SEQ ID NO:9), already contained a XbaI recognition site and the about 850 base pair PCR product was digested with restriction enzyme XbaI. The XbaI digestion product of the about 850 base pairs (insert) and the XbaI digestion product of pEX-phaZ (vector) were ligated. The composition of the ligation reaction mixture is shown below.

TABLE 6

| Insert DNA (0.3 pmol/µl) | 1 µl |
| Vector DNA (0.03 pmol/µl) | 4 µl |
| Enzyme Solution I (Included in the Kit) | 5 µl |
| Total | 10 µl |

Figure 3:
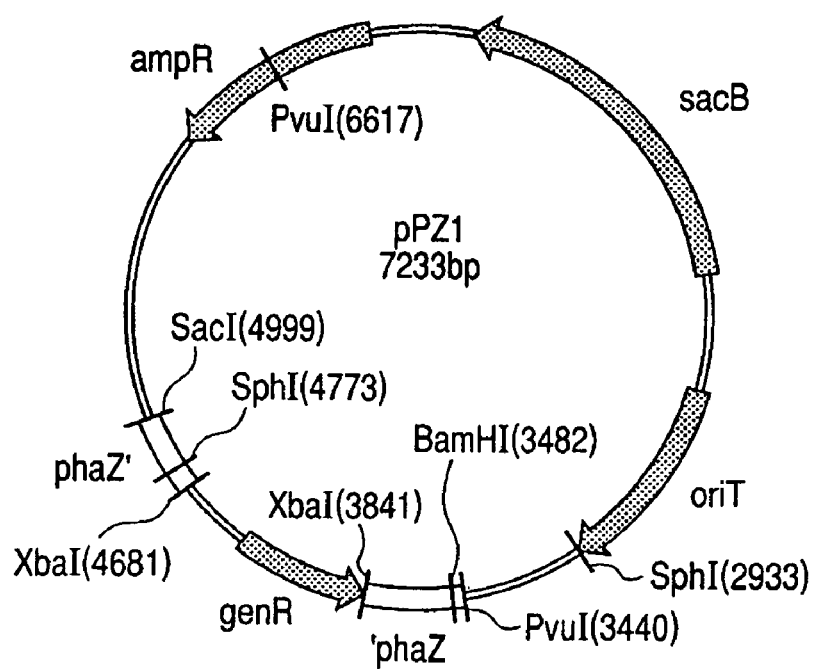
FIG. 3 is the restriction map of plasmid pPZ1 (targeting vector for the polyhydroxyalkanoate depolymerase gene) constructed in Embodiment 1.

After keeping the ligation mixture in a 16° C. incubator for 1 hour, the competent transformant cells of *Eschrichia coli* JM109 were produced. The colonies capable of growing on a LB agar plate containing 15 µg/ml of gentamicin were selected. As a result plasmid pPZ1 (SEQ ID NO:10) was obtained. The restriction map of plasmid pPZ1 (polyhydroxyalkanoate depolymerase gene targeting vector) is shown in FIG. 3.

Embodiment 2

[Acquisition of the Bacterium for Producing polyhydroxyalkanoate, *Pseudomonas* sp. PZ1 Strain (FERM BP-08571), in which the Polyhydroxyalkanoate Depolymerase Gene is Disrupted]

The mobilizing strain *Escherichia coli* S17-1 (ATCC No. 47055) was transformed by the targeting vector for the polyhydroxyalkanoate depolymerase gene (plasmid pPZ1, SEQ ID NO:10) constructed in Embodiment 1 by electroporation. The electroporation was carried out in the condition of 2.5 kV, 25 µF, 200Ω using a cell with 0.2 cm gap (Gene Pulser Cuvette 0.2 cm, BioRad Ltd.) and a commercially available electroporation device (Gene Pulser, BioRad Inc.). The S17-1 strain transformed with pPZ1, obtained as colonies capable of growing on LB agar plate containing 15 µg/ml of gentamicin, was cultured in 5 ml of LB liquid medium containing 100 µg/ml of ampicillin at 30° C. for 12 hr with shaking. Also, *Psuedomonas* species YN21 strain was cultured in 5 ml of LB liquid medium containing 100 µg/ml of ampicillin at 30° C. for 12 hr with shaking. One hundred and fifty µl of culture medium of *E. coli* S17-1 strain transformed with pPZ1 was inoculated to 150 ml of LB liquid medium containing 100 µg/ml of ampicillin and cultured at 30° C. with shaking while monitoring absorption at 600 nm (sterilized LB liquid medium was used as a control) occasionally. Similarly, 150 µl of LB liquid medium of YN21 strain was inoculated to 150 ml of LB liquid medium containing 100 µg/ml of ampicillin and cultured at 30° C. with shaking while monitoring absorption at 600 nm (sterilized LB liquid medium was used as a control) occasionally. 4.5 ml of the culture medium (absorption at 600 nm was 0.35) of pPZ1 transformed *E. coli* S17-1 strain and 0.5 ml of the culture medium (absorption at 600 nm was 0.39) of YN21 strain were mixed and filtered using a nitrocellulose filter (pore size 0.45 µm, diameter 25 mm, Millipore made, white surfactant free HATF) to collect the bacteria.

The nitrocellulose filter was place on top of an LB agar plate, keeping the face up, on which the bacteria were collected, covered with a lid to prevent drying and incubated at 30° C. for 90 min. Bacteria on the filter was suspended in 1 ml of LB liquid medium containing 100 µg/ml of ampicillin by pipetting, and an appropriate amount of the suspension was plated on a LB agar plate containing 15 µg/ml of gentamicin and 10 µg/ml of chloramphenicol. Colonies emerged after culturing at 30° C. for 2 days was streaked on a LB agar plate containing 15 µg/ml of gentamicin, 10 µg/ml of chloramphenicol and sucrose 5% (w/v) and cultured at 30° C. for 2 days. A few colonies grown on the LB agar plate containing 15 µg/ml of gentamicin, 10 µg/ml of chloramphenicol and sucrose 5% (w/v) were cultured in M9 medium containing 15 µg/ml of gentamicin, 10 µg/ml of chloramphenicol and 0.5% (w/v) of polypeptone at 30° C. for 24 hr. After harvesting the bacteria from the culture medium, the genomic DNA was prepared using Wizard Genomic DNA Purification System (Promega Inc.). PCR was carried out using the prepared genomic DNA and the control YN 21 genomic DNA (described above in 1) as templates and DNAs with sequences shown in phaZ-f1 (SEQ ID NO:2) and phaZ-r2 (SEQ ID NO:4) as primers. The following reaction mixture was prepared.

TABLE 7

| Template (genomic DNA) | 250 ng |
| Primer phaZ-f1 (SEQ ID NO: 2) | 250 pmol |
| Primer phaZ-r2 (SEQ ID NO: 4) | 250 pmol |
| 10 × buffer for amplification | 5 µl |
| dNTP | 400 µM |
| Taq polymerase (LA-Taq, Takara Bio Inc.) | 2.5 U |
| Sterilized distilled water | Appropriate amount |
| Total | 50 µl |

The PCR was carried out 30 cycles of a series of treatments of: denaturation [98° C. for 20 sec]; annealing [64° C. for 20 sec]; elongation [72° C. for 2 min]. PCR products were confirmed by agarose gel electrophoresis (gel concentration: 1 wt. %). As a result, when the genomic DNA prepared from the newly obtained colonies was used as a template, about 1.5 kb DNA fragment was amplified, and when the genomic DNA prepared from control YN21 strain was used as a template, about 690 base pair DNA fragment was. This suggests that in the newly obtained colonies, the DNA containing the gentamicin resistant gene is inserted in the middle of the polyhydroxyalkanoate depolymerase gene and the size of the DNA fragment amplified by PCR is longer by the inserted DNA, indicating the disruption of the polyhydroxyalkanoate depolymerase gene.

Embodiment 3

[PHA Production Using *Pseudomonas* sp. PZ1 Strain in which the Polyhydroxyalkanoate Depolymerase Gene is Disrupted]

PZ1 strain or control YN21 strain was inoculated in 200 ml of M9 medium containing 0.5% (w/v) of polypeptone, 0.5% (w/v) of glucose and 12 mM of 5-phenyl valeric acid (PVA), and cultured at 30° C. with shaking at a rate of 125 strokes/min. After 138 hr, the bacteria were recovered by centrifugation, washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA. The molecular weight of PHA thus obtained was measured by the gel permeation chromatography (GPC; Tosoh-HLC-8020, column: Polymer Laboratory PLgel Mixed-C (5 μm), solvent: chloroform, polystyrene conversion). PHA obtained was subjected to methanolysis by the normal procedure and then analyzed with a gas chromatography-mass spectroscopy analysis device (GC-MS, Shimadzu QP-5050, EI method) to identify the methyl ester of PHA monomer unit. These results are shown in Table 8.

TABLE 8

| Bacterial strain | PZ1 | YN21 (Control) |
| --- | --- | --- |
| Dry cell weight | 1.54[g/L] | 1.20[g/L] |
| Dry polymer weight | 1.09[g/L] | 0.59[g/L] |
| Dry polymer weight/Dry cell weight | 71% | 50% |
| Number average molecular weight | 30,000 | 35,000 |
| Weight average molecular weight | 63,000 | 85,000 |
| Monomer unit composition | | |
| 3-hydroxy-5-phenylvaleric acid | 100% | 100% |

As clearly seen in the result of Table 8, the productivity of polyhydroxyalkanoate is higher in PZ1 strain indicating that the bacterium for producing polyhydroxyalkanoate of the present invention is useful for unusual PHA production.

Embodiment 4

[PHA Production using *Pseudomonas* sp. PZ1 Strain in Which the Polyhydroxyalkanoate Depolymerase Gene is Disrupted]

PZ1 strain or control YN21 strain was inoculated in 200 ml of M9 medium containing 0.2% (w/v) of polypeptone, 0.2% (w/v) of glucose and 0.1% (v/v) of nonanoic acid, and cultured at 30° C. with shaking at a rate of 125 strokes/min. After 90 hr, the bacteria were recovered by centrifugation, washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA. The molecular weight of PHA thus obtained was measured by the gel permeation chromatography (GPC; Tosoh-HLC-8020, column: Polymer Laboratory PLgel Mixed-C (5 μm), solvent: chloroform, polystyrene conversion). PHA obtained was subjected to methanolysis by the normal procedure and then analyzed with a gas chromatography-mass spectroscopy analysis device (GC-MS, Shimadzu QP-5050, EI method) to identify the methyl ester of PHA monomer unit. These results are shown in Table 9.

TABLE 9

| Bacterial strain | PZ1 | YN21 (Control) |
| --- | --- | --- |
| Dry cell weight | 1.32[g/L] | 1.15[g/L] |
| Dry polymer weight | 0.64[g/L] | 0.48[g/L] |
| Dry polymer weight/Dry cell weight | 51% | 42% |
| Number average molecular weight | 92,000 | 109,000 |
| Weight average molecular weight | 184,000 | 209,000 |
| Monomer unit composition (area ratio) | | |
| 3-hydroxybutyric acid | 1.5% | 1.5% |
| 3-hydroxyvaleric acid | 0.8% | 0.7% |
| 3-hydroxyhexanoic acid | 0% | 0% |
| 3-hydroxyheptanoic acid | 17.2% | 23.6% |
| 3-hydroxyoctanoic acid | 0% | 0% |
| 3-hydroxynonanoic acid | 80.5% | 74.2% |
| 3-hydroxydecanoic acid | 0% | 0% |

As clearly seen in the result of Table 9, the productivity of polyhydroxyalkanoate is higher in PZ1 strain indicating that the bacterium for producing polyhydroxyalkanoate of the present invention is useful for unusual PHA production.

Embodiment 5

[PHA Production Using *Pseudomonas* sp. PZ1 Strain in Which the Polyhydroxyalkanoate Depolymerase Gene is Disrupted]

PZ1 strain or control YN21 strain was inoculated in 50 ml of M9 medium containing 0.5% (w/v) of polypeptone, 0.5% (w/v) of glucose and 12 mM of 5-phenyl valeric acid (PVA), and cultured at 30° C. with shaking at a rate of 125 strokes/min for 24, 48, 96 or 195 hr. Also, PZ1 strain or control YN21 strain was inoculated in 50 ml of M9 medium containing 0.5% (w/v) of polypeptone, 0.5% (w/v) of glucose and 12 mM of 5-phenyl valeric acid (PVA), and cultured at 30° C. with shaking at a rate of 125 strokes/min for 48 hr. Then the bacteria was recovered by centrifugation, re-suspended in 200 ml of M9 medium without carbon source and further cultured at 30° C. with shaking at a rate of 125 strokes/min for 147 hr. Each batch of bacteria was centrifuged to recover bacteria, which were washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA.

The molecular weight of PHA thus obtained was measured by the gel permeation chromatography (GPC; Tosoh-HLC-8020, column: Polymer Laboratory PLgel Mixed-C (5 μm), solvent: chloroform, polystyrene conversion). These results are shown in Table 10 and 11.

TABLE 10

| PZ1 strain, culture time [hr] | Dry cell weight (C) [g/L] | Dry polymer weight (P) [g/L] | P/C [%] | Mn | Mw |
|---|---|---|---|---|---|
| 24 | 2.50 | 1.23 | 49.4 | 64,200 | 142,400 |
| 48 | 2.49 | 1.26 | 50.4 | 62,700 | 146,900 |
| 96 | 2.44 | 1.30 | 53.4 | 64,400 | 139,200 |
| 195 | 2.14 | 1.22 | 56.9 | 60,700 | 128,000 |
| 48 + 147[Note 1] | 1.94[Note 2] | 1.15[Note 3] | 59.5 | 64,900 | 133,400 |

[Note 1] After culturing the cells for 48 hr, they were further cultured for 147 hr in a medium without a carbon source.
[Note 2] The value is standardized by the volume of the medium up to 48 hr.

TABLE 11

| YN21 strain (control), culture time [hr] | Dry cell weight (C) [g/L] | Dry polymer weight (P) [g/L] | P/C [%] | Mn | Mw |
|---|---|---|---|---|---|
| 24 | 2.27 | 1.07 | 47.1 | 67,600 | 148,400 |
| 48 | 2.27 | 1.05 | 46.3 | 79,000 | 176,700 |
| 96 | 2.39 | 1.23 | 51.5 | 71,900 | 169,400 |
| 195 | 2.02 | 1.09 | 54.0 | 72,200 | 150,400 |
| 48 + 147[Note 1] | 1.80[Note 2] | 0.89[Note 2] | 49.7 | 75,500 | 154,900 |

[Note 1] After culturing the cells for 48 hr, they were further cultured for 147 hr in a medium without a carbon source.
[Note 2] The value is standardized by the volume of the medium up to 48 hr.

PHA obtained was subjected to methanolysis by the normal procedure and then analyzed with a gas chromatography-mass spectroscopy analysis device (GC-MS, Shimadzu QP-5050$_1$ EI method) to identify the methyl ester of PHA monomer unit. The result indicated that PHA produced was a homopolymer of 3-hydroxy-5-phenyl valeric acid.

The above result clearly indicate that since the polyhydroxyalkanoate depolymerase gene is disrupted in PZ1 strain, its productivity is better than that of the conventional bacterium for producing polyhydroxyalkanoate, YN21 strain, and the PZ1 strain is useful for PHA production.

Embodiment 6

[PHA Production Using *Pseudomonas* sp. PZ1 Strain in Which the Polyhydroxyalkanoate Depolymerase Gene is Disrupted]

Each of the media was prepared by adding an alkanoic acid shown in the next Table to 50 ml of M9 medium containing 0.5% (w/v) of polypeptone and 0.5% (w/v) of glucose.

TABLE 12

| Symbol mark for the medium | Alkanoic acid added to the medium |
|---|---|
| 6-1 | 1 mM 7,8-epoxyoctanoic acid, 6 mM decanoic acid |
| 6-2 | 1 mM 4-phenoxy-n-butyric acid, 6 mM nonanoic acid |
| 6-3 | 1 mM 5-(4-fluorobenzoyl)valeric acid, 6 mM nonanoic acid |
| 6-4 | 1 mM 5-[[(4-fluorophenyl)methyl]sulfanyl]valeric acid, 6 mM nonanoic acid |
| 6-5 | 1 mM 4-(phenylsulfanyl)butyric acid, 6 mM nonanoic acid |
| 6-6 | 1 mM 5-phenylmethoxyvaleric acid, 6 mM nonanoic acid |
| 6-7 | 1 mM 5-(2-thienyl)valeric acid, 6 mM nonanoic acid |
| 6-8 | 1 mM 5-(2-thienylsulfanyl)valeric acid, 6 mM nonanoic acid |
| 6-9 | 1 mM 5-(2-thienoyl)valeric acid, 6 mM nonanoic acid |
| 6-10 | 1 mM 4-cyclohexylbutyric acid, 6 mM nonanoic acid |
| 6-11 | 1 mM 4-cyclohexyloxybutyric acid, 6 mM nonanoic acid |
| 6-12 | 1 mM 10-undecenoic acid, 6 mM nonanoic acid |
| 6-13 | 1 mM dodeca-5-enoic acid, 6 mM nonanoic acid |
| 6-14 | 1 mM 5-(methylthio)valeric acid, 6 mM nonanoic acid |

PZ1 strain or control YN21 strain was inoculated and cultured at 30° C. with shaking at a rate of 125 strokes/min for 96 hr. Each batch of the bacteria was recovered by centrifugation, washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA.

Monomer unit ratio of PHA thus obtained was measured by 1H-NMR (FT-NMR:BrunkerDP×400; resonance frequency: 400 MHz; nuclei: 1H; solvent: CDCl$_3$; reference: TMS/CDCl$_3$ in capillary; Measuring Temperature: room temperature). Result of dry polymer weight (PDW) and monomer unit ratio is shown in Table 13 (1) and (2).

TABLE 13

| Symbol mark for the medium | PZ1 PDW (g/L) | PZ1 Monomer unit ratio (mol %) | YN21 PDW (g/L) | YN21 Monomer unit ratio (mol %) |
|---|---|---|---|---|
| 6-1 | 1.43 | 3-hydroxy-7,8-epoxyoctanoic acid, 14% 3-hydroxydecanoic acid 86% | 1.08 | 3-hydroxy-7,8-epoxyoctanoic acid, 12% 3-hydroxydecanoic acid 88% |
| 6-2 | 1.38 | 3-hydroxy-4-phenoxy-n-butyric acid, 14% 3-hydroxynonanoic acid 86% | 1.05 | 3-hydroxy-4-phenoxy-n-butyric acid, 11% 3-hydroxynonanoic acid 89% |
| 6-3 | 1.25 | 3-hydroxy-5-(4-fluorobenzoyl)valeric acid 15% 3-hydroxynonanoic acid 85% | 0.87 | 3-hydroxy-5-(4-fluorobenzoyl)valeric acid 15% 3-hydroxynonanoic acid 86% |

TABLE 13-continued

| Symbol mark for the medium | PZ1 PDW (g/L) | PZ1 Monomer unit ratio (mol %) | YN21 PDW (g/L) | YN21 Monomer unit ratio (mol %) |
|---|---|---|---|---|
| 6-4 | 1.29 | 3-hydroxy-5-{[(4-fluorophenyl)methyl]sulfanyl}valeric acid 14% 3-hydroxynonanoic acid 86% | 0.89 | 3-hydroxy-5-{[(4-fluorophenyl)methyl]sulfanyl}valeric acid 14% 3-hydroxynonanoic acid 86% |
| 6-5 | 1.23 | 3-hydroxy-4-(phenylsulfanyl)butyric acid 15% 3-hydroxynonanoic acid 85% | 0.95 | 3-hydroxy-4-(phenylsulfanyl)butyric acid 12% 3-hydroxynonanoic acid 88% |
| 6-6 | 1.34 | 3-hydroxy-5-phenylmethoxyvaleric acid 14% 3-hydroxynonanoic acid 86% | 0.88 | 3-hydroxy-5-phenylmethoxyvaleric acid 12% 3-hydroxynonanoic acid 88% |
| 6-7 | 1.25 | 3-hydroxy-5-(2-thienyl)valeric acid 15% 3-hydroxynonanoic acid 85% | 0.87 | 3-hydroxy-5-(2-thienyl)valeric acid 12% 3-hydroxynonanoic acid 88% |
| 6-8 | 1.33 | 3-hydroxy-5-(2-thienylsulfanyl)valeric acid 14% 3-hydroxynonanoic acid 86% | 0.99 | 3-hydroxy-5-(2-thienylsulfanyl)valeric acid 12% 3-hydroxynonanoic acid 88% |
| 6-9 | 1.22 | 3-hydroxy-5-(2-thienoyl)valeric acid 14% 3-hydroxynonanoic acid 86% | 0.88 | 3-hydroxy-5-(2-thienoyl)valeric acid 12% 3-hydroxynonanoic acid 88% |
| 6-10 | 1.25 | 3-hydroxy-4-cyclohexylbutyric acid 14% 3-hydroxynonanoic acid 86% | 0.98 | 3-hydroxy-4-cyclohexylbutyric acid 12% 3-hydroxynonanoic acid 88% |
| 6-11 | 1.33 | 3-hydroxy-4-cyclohexyloxybutyric acid 14% 3-hydroxynonanoic acid 86% | 1.08 | 3-hydroxy-4-cyclohexyloxybutyric acid 14% 3-hydroxynonanoic acid 86% |
| 6-12 | 1.34 | 3-hydroxy-10-undecenoic acid 15% 3-hydroxynonanoic acid 85% | 1.05 | 3-hydroxy-10-undecenoic acid 14% 3-hydroxynonanoic acid 86% |
| 6-13 | 1.23 | 3-hydroxydodeca-5-enoic acid 14% 3-hydroxynonanoic acid 86% | 0.82 | 3-hydroxydodeca-5-enoic acid 13% 3-hydroxynonanoic acid 87% |
| 6-14 | 1.29 | 3-hydroxy-5-(methylthio)valeric acid 15% 3-hydroxynonanoic acid 85% | 0.91 | 3-hydroxy-5-(methylthio)valeric acid 12% 3-hydroxynonanoic acid 88% |

As clearly seen in the above result, PZ1 strain has improved productivity than the conventional bacterium for producing polyhydroxyalkanoate, YN21 strain, and thus is useful for PHA production.

Embodiment 7

[Acquisition of YN21 Strain]

M9 medium containing 0.5% of polypeptone, 0.1% of phenyl valeric acid, 0.3% of mineral solution and 1.2% of agar powder was sterilized by autoclaving. After cooling to 50° C., the medium was mixed with 0.1% of DMSO solution containing 0.05% of Nile red, distributed to sterilized Petri dish at 15 ml per dish and solidified to prepare agar medium.

The compositions of M9 medium and mineral solution are shown below.

[M9 Medium]

$Na_2HPO_4$: 6.2 g, $KH_2PO_4$: 3.0 g, NaCl: 0.5 g, $NH_4Cl$: 1.0 g (in 1 L of medkium, pH 7.0)

[Mineral Solution]

Nitrilotriacetic acid: 1.5 g, $MgSO_4$: 3.0 g, $MnSO_4$: 0.5 g, NaCl: 1.0 g, $FeSO_4$: 0.1 g, $CaCl_2$: 0.1 g, $CoCl_2$: 0.1 g, $ZnSO_4$: 0.1 g, $CuSO_4$: 0.1 g, $AlK(SO_4)_2$: 0.1 g, $H_3BO_3$: 0.1 g, $Na_2MoO_4$: 0.1 g, $NiCl_2$: 0.1 g (in 1 L, pH7.0)

Next, 5 g of soil sample collected in the field was added to 10 ml of sterilized distilled water and stirred for 1 min. 0.5 ml of this soil suspension was mixed with 4.5 ml of sterilized water and stirred to prepare 10 fold diluted solution. Similar operations were repeated to prepare 100 fold diluted solution, 1000 fold diluted solution and 10,000 fold diluted solution. The 10-10000 fold diluted sample solutions were inoculated to agar plates prepared earlier at 0.1 ml/plate and spread evenly over the surface of agar. The agar plates were transferred to incubator and cultured at 30° C. for 5 days. Among red colonies, which appeared to have produced PHA, strains with different shapes of colony were isolated. More than 10 wild strains were thus obtained. Next, 50 ml of M9 medium containing 0.5% of polypeptone, 0.5% of glucose, 0.1% of phenyl valeric acid, 0.3% of mineral solution (pH 7.0) was inoculated with each of the wild strains from the stock agar culture and cultured in a 500 ml Sakaguchi flask at 30° C. with shaking at a rate of 125 strokes/min. Also, the medium described above was adjusted to pH 5.0 or pH 8.5, and was inoculated and cultured similarly. After 72 hr, the bacteria were recovered by centrifugation, washed once with cold methanol and freeze dried. This freeze dried pellet was suspended in 10 ml of ethyl acetate, and PHA was extracted by stirring at 35° C. for 15 hr. The extract solution was filtered through a membrane filter with a pore size of 0.45 μm and then concentrated with a rotary evaporator. The concentrated solution was added to cold methanol for re-precipitation, and only the precipitate was recovered and dried in vacuo to obtain the PHA. The PHA thus obtained was weighed to measure dry polymer weight (PDW). Monomer unit ratio of the PHA was measured by 1H-NMR (FT-NMR:BrunkerDP×400; resonance frequency: 400 MHz; nuclei: 1H; solvent: $CDCl_3$; reference: TMS/CDCl3 in capillary; Measuring Temperature: room temperature). YN21 strain with PHA producing capability was obtained by comparing the dry polymer weight (PDW) and monomer unit ratio in each wild strains and existing strain.

This application claims priority from Japanese Patent Application No. 2005-023975 filed on Jan. 31, 2005, which is hereby incorporated by reference herein.

What is claimed is:

1. A bacterium for producing polyhydroxyalkanoate, in which the gene coding for the polyhydroxyalkanoate depolymerase of SEQ ID NO: 1 in *Pseudomonas* sp. YN21 (FERM BP-08569) is disrupted such that said bacterium lacks polyhydroxyalkanoate depolymerase activity.

2. *Pseudomonas* sp. PZ1 strain (FERM BP-08571) as a bacterium for producing polyhydroxyalkanoate, wherein the PZ1 strain is isogenic strain to a bacterium for producing polyhyrdoxyalkanoate, *Pseudomonas* sp. YN21 strain (FERM BP-08569) and a gene coding for the polyhydroxyalkanoate depolymerase of the PZ1 strain is disrupted.

* * * * *

UNITED STATES PATENT AND TRADEMARK OFFICE
CERTIFICATE OF CORRECTION

PATENT NO. : 7,235,396 B2
APPLICATION NO. : 11/341665
DATED : June 26, 2007
INVENTOR(S) : Nomoto et al.

It is certified that error appears in the above-identified patent and that said Letters Patent is hereby corrected as shown below:

COLUMN 1:
Line 30, "the nature" should read -- nature --.

COLUMN 2:
Line 26, "contains" should read -- contain --.

COLUMN 7:
Line 32, "Ibaragi" should read -- Ibaraki --.

COLUMN 9:
Line 57, "ariginine" should read -- arginine --.

COLUMN 22:
Line 21, "east" should read -- yeast --; and
Line 26, "the carried" should read -- then carried --.

COLUMN 26:
Line 30, "was" should read -- were --.

Signed and Sealed this

Eighth Day of April, 2008

JON W. DUDAS
*Director of the United States Patent and Trademark Office*